US 7,081,245 B2

(12) United States Patent
Murdin et al.

(10) Patent No.: US 7,081,245 B2
(45) Date of Patent: Jul. 25, 2006

(54) CHLAMYDIA ANTIGENS AND CORRESPONDING DNA FRAGMENTS AND USES THEREOF

(75) Inventors: Andrew D. Murdin, Richmond Hill (CA); Raymond P. Oomen, Aurora (CA); Joe Wang, Toronto (CA); Pamela Dunn, Woodbridge (CA)

(73) Assignee: Sanofi Pasteur Limited, Ontario (CA)

( * ) Notice: Subject to any disclaimer, the term of this patent is extended or adjusted under 35 U.S.C. 154(b) by 397 days.

(21) Appl. No.: 10/337,423

(22) Filed: Jan. 7, 2003

(65) Prior Publication Data

US 2003/0206921 A1 Nov. 6, 2003

Related U.S. Application Data

(63) Continuation of application No. 09/824,567, filed on Apr. 3, 2001, now abandoned.

(60) Provisional application No. 60/194,464, filed on Apr. 4, 2000.

(51) Int. Cl.
*A61K 39/118* (2006.01)
*C07H 21/04* (2006.01)

(52) U.S. Cl. .............................. 424/263.1; 435/320.1; 435/200.1; 435/69.1; 536/23.1; 536/23.7

(58) Field of Classification Search .................. 435/6, 435/91.1, 91.2; 536/23.1, 24.3; 530/300
See application file for complete search history.

(56) References Cited

U.S. PATENT DOCUMENTS

| 5,474,796 | A | 12/1995 | Brennan |
| 6,403,101 | B1 | 6/2002 | Murdin et al. |
| 6,559,294 | B1 | 5/2003 | Griffais et al. |
| 6,822,071 | B1 * | 11/2004 | Stephens et al. ............ 530/300 |
| 2004/0005667 | A1 * | 1/2004 | Ratti et al. .................. 435/69.3 |

FOREIGN PATENT DOCUMENTS

| WO | WO 99/27105 | 6/1999 |
| WO | WO 02/02606 | 2/2002 |

OTHER PUBLICATIONS

Grayston et al. (1995) *Journal of Infectious Diseases* 168:1231.
Campos et al. (1995) *Investigation of Ophthalmology and Visual Science* 36:1477.
Grayston et al. (1990) Journal of Infectious Diseases 161:618.
Marrie (1993) *Clinical Infectious Diseases* 18:501.
Wang et al. (1986) Chlamydial infections, Cambridge University Press, Cambridge. p. 329.
Saikku et al. (1988) *Lancet*; ii:983.
Thom et al. (1992) *JAMA* 268:68.
Linnanmaki et al. (1993), *Circulation* 87:1130.
Saikku et al. (1992) *Annals Internal Medicine* 116:273.
Melnick et al. (1993) *American Journal of Medicine* 95:499.
Shor et al. (1992) *South African. Medical Journal* 82:158.
Kuo et al. (1993) *Journal of Infectious Diseases* 167:841.
Kuo et al. (1993) *Arteriosclerosis and Thrombosis* 13:1501.
Campbell et al. (1995) *Journal of Infectious Diseases* 172:585.
Chiu et al. (1997) *Circulation* 96 (7) :2144-2148.
Ramirez et al. (1996) *Annals of Internal Medicine* 125:979.
Jackson et al. Abst. K121, p272, 36th ICAAC, Sep. 15-18, 1996, New Orleans.
Fong et al. (1997) *Journal of Clinical Microbiolology* 35:48.
Hahn et al., "Evidence for *Chlamydia pneumoniae* infection in steroid-dependent asthma," *Ann Allergy Asthma Immunol*. Jan. 1998; 80(1):45-49.
Hahn et al., "Association of *Chlamydia pneumoniae* IgA antibodies with recently symptomatic asthma," *Epidemiol Infect*. Dec. 1996; 117(3):513-517.
Bjornsson et al., "Serology of chlamydia in relation to asthma and bronchial hyperresponsiveness," *Scand J Infect Dis*. 1996; 28(1): 63-69.
Hahn, "Treatment of *Chlamydia pneumoniae* infection in adult asthma: a before-after trial," J Fam Pract. Oct. 1995; 41(4): 345-351.

(Continued)

*Primary Examiner*—Jeanine A. Goldberg
(74) *Attorney, Agent, or Firm*—Foley & Lardner LLP

(57) ABSTRACT

The present invention provides nucleic acids, proteins and vectors for a method of nucleic acid, including DNA, immunization of a host, including humans, against disease caused by infection by a strain of *Chlamydia*, specifically *C. pneumoniae*. The method employs a vector containing a nucleotide sequence encoding an ATP-binding cassette of a strain of *Chlamydia pneumoniae* and a promoter to effect expression of the ATP-binding cassette gene product in the host. Modifications are possible within the scope of this invention.

33 Claims, 11 Drawing Sheets

OTHER PUBLICATIONS

Allegra et al., "Acute exacerbations of asthma in adults," role of *Chlamydia pneumoniae infection*, Eur Respit J. Dec. 1994; 7 (12) : 2165-2168.

Hahn et al., "Association of *Chlamydia pneumoniae* (strain TWAR) infection with wheezing, asthmatic bronchitis, and adultonset asthma," *JAMA*. Jul. 10, 1991; 266(2): 225-230.

Pal et al., (1996) *Infection and Immunity*. 64:5341.

Jones et al. (1995) *Vaccine* 13:715.

Igietseme et al. (1993) *Regional Immunology* 5:317.

Magee et al. (1993) *Regional Immunology* 5:305.

Landers et al. (1991) *Infection & Immunity* 59:3774.

Magee et al. (1995) *Infection & Immunity* 63:516.

Cotter et al. (1995) *Infection and Immunity* 63:4704.

Campbell et al (1990) *Infection and Immunity* 58:93.

McCafferty et al. (1995) *Infection and Immunity* 63:2387-9.

Gaydos et al.; "Similarity of *Chlamydia pneumoniae* strains in the Variable Domain IV Region of the Major Outer Membrane Protein Gene," *Infection and Immunity*; 60(12):5319-5323, Dec. 1992.

Wiedmann-A1-Ahmad M, et al. "Reactions of polyclonal and neutralizing anti-p54 monoclonal antibodies with an isolated, species-specific 54-kilodalton protein of *Chlamydia pneumoniae*," *Clin Diagn Lab Immunol*. 1997, (6:700-704).

Hughes et al., 1992. *Infect. Immun.* 60 (9) :3497.

Dion et al., 1990. *Virology* 179:474-477.

Snijders et al., 1991. *J. Gen. Virol.* 72:557-565.

Langeveld et al., *Vaccine* 12 (15) :1473-1480, 1994.

Kunkel et al., *Proc. Natl. Acad. Sci.* USA (1985) 82:488.

Casey & Davidson, *Nucl. Acid Res.* (1977) 4:1539.

Cagnon et al., *Protein Engineering* (1991) 4(7):843.

Takase et al., *J. Bact.* (1987) 169:5692.

Perez Melgosa et al., *Infect Immun* (1994) 62:880.

Watson et al., *Nucleic Acids Res* (1990) 18:5299.

Watson et al., *Microbiology* (1995) 141:2489.

Melgosa et al., *FEMS Microbiol Lett* (1993) 112 :199.

Campbell et al., *J Clin Microbiol* (1990) 28 :1261.

Iijima et al., *J Clin Microbiol* (1994) 32:583.

Http://chlamydia-www.berkeley.edu:4231/.

Bachmaier et al., *Science* (1999) 283:1335.

Ausubel et al.; "Current Protocols in Molecular Biology," John Wiley & Sons Inc.; vol. 1; 1993; 15 sheets.

Silhavy et al., "Experiments with Gene Fusions," *Cold Spring Harbor Laboratory Press*; 1984; pp. 191-195.

Davis et al., "A Manual for Genetic Engineering: Advanced Bacterial Genetics" *Cold Spring Harbor Laboratory Press*; 1980; pp. 174-176.

Jackson et al., "Isolation of *Chlamydia pneumoniae* from a Carotid Endarterectomy Specimen" *The Journal of Infectious Diseases* (1997) 176:292-295.

Laitinen et al., "*Chlamydia pneumoniae* Infection Induces Inflammatory Changes in the Aorta of Rabbits" *Infection and Immunity*, Nov. 1997, vol. 65, No. 11, pp. 4832-4835.

Rottenberg et al., "Role of Innate and Adaptive Immunity in the Outcome of Primary Infection with *Chlamydia pneumoniae*, as Analyzed in Genetically Modified Mice," *The Journal of Immunology* (1999), 162:2829-2836.

Penttila et al., "Depletion of CD8* cells abolishes memory in acquired immunity against *Chlamydia pneumoniae* in BALB/c mice" *Immunology* (1999) 97:490-496.

Knudsen et al., "Identification of Two Novel Genes Encoding 97- to 99-Kilodalton Outer Membrane Proteins of *Chlamydia pneumoniae*" *Infection and Immunity*, Jan. 1999, vol. 67, No. 1, pp. 375-383.

Parker et al., "Peptide Binding to MHC Class I Molecules: Implications for Antigenic Peptide Prediction" *Immunol Res* (1995) 14:34-57.

Kalman, S. et al., "Comparative Genomes of *Chlamydia peneumoniae* and *C. trachomatis*," *Nature Genetics* (Apr. 1999), vol. 21, No. 4, pp. 385-389, XP000856693.

Kalman et al., "*Chlamydia pneumoniae* section 22 of 103 of the complete genome," retrieved from *Chlamydophila pneumoniae* CWL029; EMBL, Heidelberg, FRG Mar. 15, 1999; database accession No. AE001606; XP002191845.

Kalman et al., "Oligopeptide binding protein OPPA_1 or CPN0195 or CP0572", retrieved from *Chlamydophila pneumoniae* database accession No. Q9Z8Y9; XP00219846.

Puolakkainen & Makela, "Vaccination against infections by *Chlamydia pneumoniae*," *Comptes Rendus des Seances de L-Academie des Sciences Serie III* (Nov. 1999), vol. 322, No. 11, pp. 973-978.

Svanholm et al., "Enhancement of antibody responses by DNA immunization using expression vectors mediating efficient antigen secretion," *J. Immunol. Methods* (Aug. 1999), vol. 228, No. 1-2, pp. 121-130, XP000881871.

Svanholm et al., "Protective DNA immunization against *Chlamydia pneumoniae*," *Scandinavian Journal of Immunology* (Apr. 2000), vol. 51, No. 4, pp. 345-353, XP002191683.

Murdin et al., "Use of a mouse lung challenge model to identify antigens protective against *Chlamydia pneumoniae* lung infection," *J. Infectious Diseases* (Jun. 2000), vol. 181, No. suppl. 3, pp. S544-S551, XP000997839.

Wishart et al., "SEQSEE: a comprehensive program suite for protein sequence analysis" (1994) *CABIOS* vol. 10, No. 2, pp. 121-132.

* cited by examiner

Figure 1. Sequence of *C. pneumoniae* ATP-binding cassette gene (SEQ ID NO:1)

```
acttcccccc tgctaaacta tgctcagata atgctgctat gattgcaggt ctagggggag 60
aaaattttca aaaaaactct agtattccgg aaattcgtat atg cgc aag ata tca   115
                                           Met Arg Lys Ile Ser
                                             1               5 gtg gga atc tgt atc acc att ctc ctt agc ctc tcc gta gtc ctc caa   163
Val Gly Ile Cys Ile Thr Ile Leu Leu Ser Leu Ser Val Val Leu Gln
                 10                  15                  20 ggc tgc aag gag tcc agt cac tcc tct aca tct cgg gga gaa ctc gct   211
Gly Cys Lys Glu Ser Ser His Ser Ser Thr Ser Arg Gly Glu Leu Ala
             25                  30                  35 att aat ata aga gat gaa ccc cgt tct tta gat cca aga caa gtg cga   259
Ile Asn Ile Arg Asp Glu Pro Arg Ser Leu Asp Pro Arg Gln Val Arg
         40                  45                  50 ctt ctt tca gaa atc agc ctt gtc aaa cat atc tat gag gga tta gtt   307
Leu Leu Ser Glu Ile Ser Leu Val Lys His Ile Tyr Glu Gly Leu Val
     55                  60                  65 caa gaa aat aat ctt tca gga aat ata gag cct gct ctt gca gaa gac   355
Gln Glu Asn Asn Leu Ser Gly Asn Ile Glu Pro Ala Leu Ala Glu Asp
 70                  75                  80                  85 tac tct ctt tcc tcg gac gga ctc act tat act ttt aaa ctg aaa tca   403
Tyr Ser Leu Ser Ser Asp Gly Leu Thr Tyr Thr Phe Lys Leu Lys Ser
                 90                  95                 100 gct ttt tgg agt aat ggc gac ccc tta aca gct gaa gac ttt ata gaa   451
Ala Phe Trp Ser Asn Gly Asp Pro Leu Thr Ala Glu Asp Phe Ile Glu
            105                 110                 115 tct tgg aaa caa gta gct act caa gaa gtc tca gga atc tat gct ttt   499
Ser Trp Lys Gln Val Ala Thr Gln Glu Val Ser Gly Ile Tyr Ala Phe
        120                 125                 130 gcc ttg aat cca att aaa aat gta cga aag atc caa gag gga cac ctc   547
Ala Leu Asn Pro Ile Lys Asn Val Arg Lys Ile Gln Glu Gly His Leu
    135                 140                 145 tcc ata gac cat ttt gga gtg cac tct cct aat gaa tct aca ctt gtt   595
Ser Ile Asp His Phe Gly Val His Ser Pro Asn Glu Ser Thr Leu Val
150                 155                 160                 165 gtt acc ctg gaa tcc cca acc tcg cat ttc tta aaa ctt tta gct ctt   643
Val Thr Leu Glu Ser Pro Thr Ser His Phe Leu Lys Leu Leu Ala Leu
                170                 175                 180
```

Figure 1 Cont.

```
cca gtc ttt ttc ccc gtt cat aaa tct caa aga acc ctg caa tcc aaa     691
Pro Val Phe Phe Pro Val His Lys Ser Gln Arg Thr Leu Gln Ser Lys
            185                 190                 195 tct cta cct ata gca agc gga gct ttc tat cct aaa aat atc aaa caa     739
Ser Leu Pro Ile Ala Ser Gly Ala Phe Tyr Pro Lys Asn Ile Lys Gln
            200                 205                 210 aaa caa tgg ata aaa ctc tca aaa aac cct cac tac tat aat caa agt     787
Lys Gln Trp Ile Lys Leu Ser Lys Asn Pro His Tyr Tyr Asn Gln Ser
            215                 220                 225 cag gtg gaa act aaa acg att acg att cac ttc att ccc gat gca aac     835
Gln Val Glu Thr Lys Thr Ile Thr Ile His Phe Ile Pro Asp Ala Asn
230                 235                 240                 245 aca gca gca aaa cta ttt aat cag gga aaa ctc aat tgg caa gga cct     883
Thr Ala Ala Lys Leu Phe Asn Gln Gly Lys Leu Asn Trp Gln Gly Pro
            250                 255                 260 cct tgg gga gaa cgc att cct caa gaa acc cta tcc aat tta cag tct     931
Pro Trp Gly Glu Arg Ile Pro Gln Glu Thr Leu Ser Asn Leu Gln Ser
            265                 270                 275 aag ggg cac tta cac tct ttt gat gtc gca gga acc tca tgg ctc acc     979
Lys Gly His Leu His Ser Phe Asp Val Ala Gly Thr Ser Trp Leu Thr
            280                 285                 290 ttc aat atc aat aaa ttc ccc ctc aac aat atg aag ctt aga gaa gcc    1027
Phe Asn Ile Asn Lys Phe Pro Leu Asn Asn Met Lys Leu Arg Glu Ala
            295                 300                 305 tta gca tca gcc tta gat aag gaa gct ctt gtc tca act ata ttc tta    1075
Leu Ala Ser Ala Leu Asp Lys Glu Ala Leu Val Ser Thr Ile Phe Leu
310                 315                 320                 325 ggc cgt gca aaa act gcc gat cat ctc cta cct aca aat att cat agc    1123
Gly Arg Ala Lys Thr Ala Asp His Leu Leu Pro Thr Asn Ile His Ser
            330                 335                 340 tat ccc gaa cat caa aaa caa gag atg gca caa cgc caa gct tac gct    1171
Tyr Pro Glu His Gln Lys Gln Glu Met Ala Gln Arg Gln Ala Tyr Ala
            345                 350                 355 aaa aaa ctc ttt aaa gaa gct tta gaa gaa ctc caa atc act gct aaa    1219
Lys Lys Leu Phe Lys Glu Ala Leu Glu Glu Leu Gln Ile Thr Ala Lys
            360                 365                 370 gat ctc gaa cat ctt aat ctt atc ttt ccc gtt tcc tcg tca gca agt    1267
Asp Leu Glu His Leu Asn Leu Ile Phe Pro Val Ser Ser Ser Ala Ser
375                 380                 385
```

Figure 1 Cont.

```
tct tta cta gtc caa ctt ata cga gaa cag tgg aaa gaa agt tta ggg   1315
Ser Leu Leu Val Gln Leu Ile Arg Glu Gln Trp Lys Glu Ser Leu Gly
390             395             400             405 ttc gct atc cct att gtc gga aag gaa ttt gct ctt ctc caa gca gac   1363
Phe Ala Ile Pro Ile Val Gly Lys Glu Phe Ala Leu Leu Gln Ala Asp
            410             415             420 cta tct tca ggg aac ttc tct tta gct aca gga gga tgg ttc gca gac   1411
Leu Ser Ser Gly Asn Phe Ser Leu Ala Thr Gly Gly Trp Phe Ala Asp
        425             430             435 ttt gct gat cct atg gca ttt cta acg atc ttt gct tat cca tca gga   1459
Phe Ala Asp Pro Met Ala Phe Leu Thr Ile Phe Ala Tyr Pro Ser Gly
        440             445             450 gtt cct cct tat gca atc aac cat aag gac ttc cta gaa att cta caa   1507
Val Pro Pro Tyr Ala Ile Asn His Lys Asp Phe Leu Glu Ile Leu Gln
    455             460             465 aac ata gaa caa gag caa gat cac caa aaa cgc tcg gaa tta gtg tcg   1555
Asn Ile Glu Gln Glu Gln Asp His Gln Lys Arg Ser Glu Leu Val Ser
470             475             480             485 caa gct tct ctt tac cta gag acc ttt cat att att gag ccg atc tac   1603
Gln Ala Ser Leu Tyr Leu Glu Thr Phe His Ile Ile Glu Pro Ile Tyr
            490             495             500 cac gac gca ttt caa ttt gct atg aat aaa aaa ctt tct aat cta gga   1651
His Asp Ala Phe Gln Phe Ala Met Asn Lys Lys Leu Ser Asn Leu Gly
            505             510             515 gtc tca cca aca gga gtt gtg gac ttc cgt tat gct aag gaa aat       1696
Val Ser Pro Thr Gly Val Val Asp Phe Arg Tyr Ala Lys Glu Asn
        520             525             530 tagcacctct tttaatctcg caaacttgtc aagaactgaa tcttatacta aactgggtgc   1756
ctttgtggca cctcgtttcc ttctgactgc tcttctctct cta                     1799
```

Figure 2. Restriction enzyme analysis of the *C. pneumoniae* ATP-binding cassette gene (SEQ ID NO:1)

```
                                     BseMII   CviRI
                        Hpy188IX     BspMI|   HaeIV
                         DdeI  |   Fnu4HI ||  Hin4I
                      BbvI  |  |    TseI| || MwoI  |   BfaI
                         |  |  |       || ||    |  |      |
      ACTTCCCCCCTGCTAAACTATGCTCAGATAATGCTGCTATGATTGCAGGTCTAGGGGGAG
    1 ---------+---------+---------+---------+---------+---------+ 60
      TGAAGGGGGGACGATTTGATACGAGTCTATTACGACGATACTAACGTCCAGATCCCCCTC

ApoI
                              Tsp509I
                        Hpy178III   |
      XmnI                   MspI   |
    ApoI |                 BsaWI|   |          HhaI             HinfI
 Tsp509I |            BfaI Kpn2I|   |         FspI| EcoRV        TfiI
       | |               |      ||  |            ||     |       TspRI
                                                                  |
      AAAATTTTCAAAAAAACTCTAGTATTCCGGAAATTCGTATATGCGCAAGATATCAGTGGG
   61 ---------+---------+---------+---------+---------+---------+ 120
      TTTTAAAAGTTTTTTTGAGATCATAAGGCCTTTAAGCATATACGCGTTCTATAGTCACCC CviRI    MaeIII
                                                   MnlI|    Tsp45I
                                                Fnu4HI||   BspGI |
                         CviJI             BsaJI     |||    BsrI |
                    Bpu10I   |          MnlI    |CviJI|||  BseRI | |
   HphI               DdeI   |      BbvI   |  StyI TseI|||HinfI| | |
      |                  |   |         |   |     |    ||||    | | | |
      AATCTGTATCACCATTCTCCTTAGCCTCTCCGTAGTCCTCCAAGGCTGCAAGGAGTCCAG
  121 ---------+---------+---------+---------+---------+---------+ 180
      TTAGACATAGTGGTAAGAGGAATCGGAGAGGCATCAGGAGGTTCCGACGTTCCTCAGGTC Sth132I
                                                           AlwI |
       Sth132I   MnlI              MseI                    CjeI |
   PleI      |   AvaI|             VspI               BscGI   | |
      |      |      ||                |                   |   | |
      TCACTCCTCTACATCTCGGGGAGAACTCGCTATTAATATAAGAGATGAACCCCGTTCTTT
  181 ---------+---------+---------+---------+---------+---------+ 240
      AGTGAGGAGATGTAGAGCCCCTCTTGAGCGATAATTATATTCTCTACTTGGGGCAAGAAA DpnI
  BstYI |                      CjeI                   MslI
 Sau3AI |               Hpy188IX | CviJI          MnlI |Tth111II
      | |                      | |     |             | |       |
      AGATCCAAGACAAGTGCGACTTCTTTCAGAAATCAGCCTTGTCAAACATATCTATGAGGG
  241 ---------+---------+---------+---------+---------+---------+ 300
      TCTAGGTTCTGTTCACGCTGAAGAAAGTCTTTAGTCGGAACAGTTTGTATAGATACTCCC
```

Figure 2 Cont.

```
                                       Cac8I
    Hpy178III        Hpy178III     CviJI |   CviRI        BbsI
         |                |            | |      |           |
         ATTAGTTCAAGAAAATAATCTTTCAGGAAATATAGAGCCTGCTCTTGCAGAAGACTACTC
 301 ---------+---------+---------+---------+---------+---------+ 360
         TAATCAAGTTCTTTTATTAGAAAGTCCTTTATATCTCGGACGAGAACGTCTTCTGATGAG

Hpy188IX
                PleI|
         BsaJI  ||    MnlI           DraI            AluI
     MboII  |   ||HinfI|            MseI|            CviJI
        |   |   ||    ||              ||               |
         TCTTTCCTCGGACGGACTCACTTATACTTTTAAACTGAAATCAGCTTTTTGGAGTAATGG
 361 ---------+---------+---------+---------+---------+---------+ 420
         AGAAAGGAGCCTGCCTGAGTGAATATGAAAATTTGACTTTAGTCGAAAAACCTCATTACC AluI                                 Hpy178III
                  CviJI          HinfI                   SmlI  |
                  MspA1I         MboII Bce83I          AluI    |  |
      SimI   MseI PvuII          BbsI  TfiI  Eco57I    CviJI   |  |
        |      |     |              |     |     |         |   |  |
         CGACCCCTTAACAGCTGAAGACTTTATAGAATCTTGGAAACAAGTAGCTACTCAAGAAGT
 421 ---------+---------+---------+---------+---------+---------+ 480
         GCTGGGGAATTGTCGACTTCTGAAATATCTTAGAACCTTTGTTCATCGATGAGTTCTTCA DpnI
       HinfI                                             MnlI|
         TfiI                         MseI              BstYI||
         BsmAI |                  Tsp509I     |         Sau3AI||
    Hpy178III| |                   HinfI      |          AlwI |||
         DdeI ||  |   BseMII        TfiI      |          RsaI| |||
          | || |    |                |        |             || |||
         CTCAGGAATCTATGCTTTTGCCTTGAATCCAATTAAAAATGTACGAAAGATCCAAGAGGG
 481 ---------+---------+---------+---------+---------+---------+ 540
         GAGTCCTTAGATACGAAAACGGAACTTAGGTTAATTTTTACATGCTTTCTAGGTTCTCCC BseSI
                                 BsiHKAI
                                 Bsp1286I
                                 CviRI   |                     BsaJI
            MnlI                 MjaIV   |      HinfI          EcoRII
            BsmFI †       ApaLI  |  |              TfiI      MaeIII  |
             | |              |  |  |              |              |  |
         ACACCTCTCCATAGACCATTTTGGAGTGCACTCTCCTAATGAATCTACACTTGTTGTTAC
 541 ---------+---------+---------+---------+---------+---------+ 600
         TGTGGAGAGGTATCTGGTAAAACCTCACGTGAGAGGATTACTTAGATGTGAACAACAATG
```

Figure 2 Cont.

```
                              AluI
        HinfI                 CviJI    EarI
         TfiI         MseI    CjePI |  SapI
   ScrFI |            MnlI| MboII | |  BsrI|       BscGI
     | |              | |    | | |   | ||           |
     CCTGGAATCCCCAACCTCGCATTTCTTAAAACTTTTAGCTCTTCCAGTCTTTTTCCCCGT
 601 ---------+---------+---------+---------+---------+---------+ 660
     GGACCTTAGGGGTTGGAGCGTAAAGAATTTTGAAAATCGAGAAGGTCAGAAAAAGGGGCA AluI
                                                      CviJI
                                               MwoI    |
                                               AciI |  |
 Sth132I CjePI         CviRI           SfcI    Cac8I| |  |
    |      |             |               |       | | |  |
     TCATAAATCTCAAAGAACCCTGCAATCCAAATCTCTACCTATAGCAAGCGGAGCTTTCTA
 661 ---------+---------+---------+---------+---------+---------+ 720
     AGTATTTAGAGTTTCTTGGGACGTTAGGTTTAGAGATGGATATCGTTCGCCTCGAAAGAT Tth111II                               MnlI
                       |                                     |
     TCCTAAAAATATCAAACAAAAACAATGGATAAAACTCTCAAAAAACCCTCACTACTATAA
 721 ---------+---------+---------+---------+---------+---------+ 780
     AGGATTTTTATAGTTTGTTTTTGTTACCTATTTTGAGAGTTTTTTGGGAGTGATGATATT Sth132I   Fnu4HI
                        HinfI   Hpy178III          |     TseI|
                         TfiI SfaNI       | CviRI| MwoI   ||
                           |    |         |   ||    |    ||
     TCAAAGTCAGGTGGAAACTAAAACGATTACGATTCACTTCATTCCCGATGCAAACACAGC
 781 ---------+---------+---------+---------+---------+---------+ 840
     AGTTTCAGTCCACCTTTGATTTTGCTAATGCTAAGTGAAGTAAGGGCTACGTTTGTGTCG AvaII           MnlI
                                 EcoO109I      Bce83I |
              MseI               Psp5II        BslI|  |
               BbvI|    MunI     Sau96I  BsaJI  ||   | BsmI
     Tth111II   ||     Tsp509I  Sse8647I  StyI  ||   | XmnI
         |     ||       |         |        | ·||  |    |
     AGCAAAACTATTTAATCAGGGAAAACTCAATTGGCAAGGACCTCCTTGGGGAGAACGCAT
 841 ---------+---------+---------+---------+---------+---------+ 900
     TCGTTTTGATAAATTAGTCCCTTTTGAGTTAACCGTTCCTGGAGGAACCCCTCTTGCGTA BseSI
  Hpy178III     Tsp509I       DdeI Bsp1286I
     SmlI |    MnlI      |  Bst4CI   |  BmgI |
      | |      |         |    | |       |  |
     TCCTCAAGAAACCCTATCCAATTTACAGTCTAAGGGGCACTTACACTCTTTTGATGTCGC
 901 ---------+---------+---------+---------+---------+---------+ 960
     AGGAGTTCTTTGGGATAGGTTAAATGTCAGATTCCCCGTGAATGTGAGAAAACTACAGCG
```

Figure 2 Cont.

```
                                                                DdeI
            MnlI                                                AluI|
         CviJI |                                                CviJI|
       NlaIII| |                                              HindIII ||
       HphI  || |                       ApoI                    MnlI   | ||
   NlaIV |   || |                     Tsp509I                   |      | ||
     |   |   || |                        |                      |      | ||
      AGGAACCTCATGGCTCACCTTCAATATCAATAAATTCCCCCTCAACAATATGAAGCTTAG
 961  ---------+---------+---------+---------+---------+---------+ 1020
      TCCTTGGAGTACCGAGTGGAAGTTATAGTTATTTAAGGGGGAGTTGTTATACTTCGAATC Bpu10I         SfaNI                                    CviJI
        DdeI          DdeI|         AluI      BcefI           HaeIII
       CviJI |        CviJI||       CviJI     BsmAI            DdeI    |
         |   |          | ||          |         |               |      |
      AGAAGCCTTAGCATCAGCCTTAGATAAGGAAGCTCTTGTCTCAACTATATTCTTAGGCCG
 1021 ---------+---------+---------+---------+---------+---------+ 1080
      TCTTCGGAATCGTAGTCGGAATCTATTCCTTCGAGAACAGAGTTGATATAAGAATCCGGC DpnI
          Sau3AI  |                            Hpy178III
        BstAPI  | |                              AluI    |Sth132I
    CviRI  MwoI | |              SspI   CviJI    |CjeI   |
      |    |   | |                |      |       | |    |
      TGCAAAAACTGCCGATCATCTCCTACCTACAAATATTCATAGCTATCCCGAACATCAAAA
 1081 ---------+---------+---------+---------+---------+---------+ 1140
      ACGTTTTTGACGGCTAGTAGAGGATGGATGTTTATAAGTATCGATAGGGCTTGTAGTTTT AluI
                           CjeI                       CviJI
                           AluI |                   HindIII |
                          CviJI |                      DraI | |
           BccI         HindIII | |                    MseI| | |
             |             |    | |                      || | |
      ACAAGAGATGGCACAACGCCAAGCTTACGCTAAAAAACTCTTTAAAGAAGCTTTAGAAGA
 1141 ---------+---------+---------+---------+---------+---------+ 1200
      TGTTCTCTACCGTGTTGCGGTTCGAATGCGATTTTTTGAGAAATTTCTTCGAAATCTTCT TaqI
              Hpy178III|
                  DpnI ||
               BglII | ||
               BstYI | ||
              Sau3AI | ||
             TspRI | | ||
             BtsI  | | ||                           Sth132I
       MboII  |    | | ||       MseI        BscGI     |
         |    |    | | ||         |           |       |
      ACTCCAAATCACTGCTAAAGATCTCGAACATCTTAATCTTATCTTTCCCGTTTCCTCGTC
 1201 ---------+---------+---------+---------+---------+---------+ 1260
      TGAGGTTTAGTGACGATTTCTAGAGCTTGTAGAATTAGAATAGAAAGGGCAAAGGAGCAG
```

Figure 2 Cont.

```
                                      MmeI
           BfaI                       TspRI |
  MnlI     SpeI|            Bst4CI    | |        MmeI
  |        | |              |         | |        |
      AGCAAGTTCTTTACTAGTCCAACTTATACGAGAACAGTGGAAAGAAAGTTTAGGGTTCGC
1261  ---------+---------+---------+---------+---------+---------+ 1320
      TCGTTCAAGAAATGATCAGGTTGAATATGCTCTTGTCACCTTTCTTTCAAATCCCAAGCG

ApoI
                      MboII
                      Tsp509I         EarI
           Hpy188IX   |                Eco57I
           BslI   |   |                SapI  MboII     Tth111II
           | |   |   |                |    |         |
      TATCCCTATTGTCGGAAAGGAATTTGCTCTTCTCCAAGCAGACCTATCTTCAGGGAACTT
1321  ---------+---------+---------+---------+---------+---------+ 1380
      ATAGGGATAACAGCCTTTCCTTAAACGAGAAGAGGTTCGTCTGGATAGAAGTCCCTTGAA

DpnI
                                      Sau3AI  |
        SfcI                  AlwI    |  |
        AluI|                 BstAPI  |  |
        CviJI|       DrdII    MwoI    |  |            DpnI
        MnlI|        BccI  |  FokI |  |  |            Sau3AI  |
        | |          | |     | |     | |              | |
      CTCTTTAGCTACAGGAGGATGGTTCGCAGACTTTGCTGATCCTATGGCATTTCTAACGAT
1381  ---------+---------+---------+---------+---------+---------+ 1440
      GAGAAATCGATGTCCTCCTACCAAGCGTCTGAAACGACTAGGATACCGTAAAGATTGCTA

CjeI                    ApoI
           Hpy178III            MnlI  |                 Tsp509I
  CjeI     BccI   |             CviRI|  |               BfaI    |
  |        |  |                 | |   |                 |       |
      CTTTGCTTATCCATCAGGAGTTCCTCCTTATGCAATCAACCATAAGGACTTCCTAGAAAT
1441  ---------+---------+---------+---------+---------+---------+ 1500
      GAAACGAATAGGTAGTCCTCAAGGAGGAATACGTTAGTTGGTATTCCTGAAGGATCTTTA

AluI
                  DpnI                                  CviJI
                  Sau3AI |                              Cac8I  |
                  CjePI  |  |           Tsp509I         HindIII|
              HphI  |   |  |            Hpy188IX|       CjePI| |
              |    | |   |               | |            | | |
      TCTACAAAACATAGAACAAGAGCAAGATCACCAAAAACGCTCGGAATTAGTGTCGCAAGC
1501  ---------+---------+---------+---------+---------+---------+ 1560
      AGATGTTTTGTATCTTGTTCTCGTTCTAGTGGTTTTTGCGAGCCTTAATCACAGCGTTCG
```

Figure 2 Cont.

```
              BfaI                                DpnI
          BsaI    |                            Sau3AI |                   HgaI
          BsmAI   |                            CviJI| |                   Tsp509I
            |  |                                 | | |                      |
          TTCTCTTTACCTAGAGACCTTTCATATTATTGAGCCGATCTACCACGACGCATTTCAATT
     1561 ---------+---------+---------+---------+---------+---------+ 1620
          AAGAGAAATGGATCTCTGGAAAGTATAATAACTCGGCTAGATGGTGCTGCGTAAAGTTAA

HinfI
                                     CjeI|
                            HphI     | |         PleI
                         BfaI|       | |      BsmAI|               MjaIV
                            || ||           ||                       |
          TGCTATGAATAAAAAACTTTCTAATCTAGGAGTCTCACCAACAGGAGTTGTGGACTTCCG
     1621 ---------+---------+---------+---------+---------+---------+ 1680
          ACGATACTTATTTTTTGAAAGATTAGATCCTCAGAGTGGTTGTCCTCAACACCTGAAGGC Bpu10I
             DdeI                         MnlI               HinfI
          CjeI  |Tsp509I          MseI    |      Hpy178III   TfiI  TaqII
            |   |    |              |     |          |         |     |
          TTATGCTAAGGAAAATTAGCACCTCTTTTAATCTCGCAAACTTGTCAAGAACTGAATCTT
     1681 ---------+---------+---------+---------+---------+---------+ 1740
          AATACGATTCCTTTTAATCGTGGAGAAAATTAGAGCGTTTGAACAGTTCTTGACTTAGAA NlaIV        NlaIV
                  BsrI|        BanI   |    Hpy188IX
                  BanI||       BglI | |       MboII|          EarI
                  BmrI|||      MwoI | |       MnlI ||         SapI
                     | |||        | | |          | ||           |
          ATACTAAACTGGGTGCCTTTGTGGCACCTCGTTTCCTTCTGACTGCTCTTCTCTCTCTA
     1741 ---------+---------+---------+---------+---------+--------- 1799
          TATGATTTGACCCACGGAAACACCGTGGAGCAAAGGAAGACTGACGAGAAGAGAGAGAT
```

Construction of pCACPNM209

Figure 4: Protective efficacy of DNA immunization with pCACPNM209
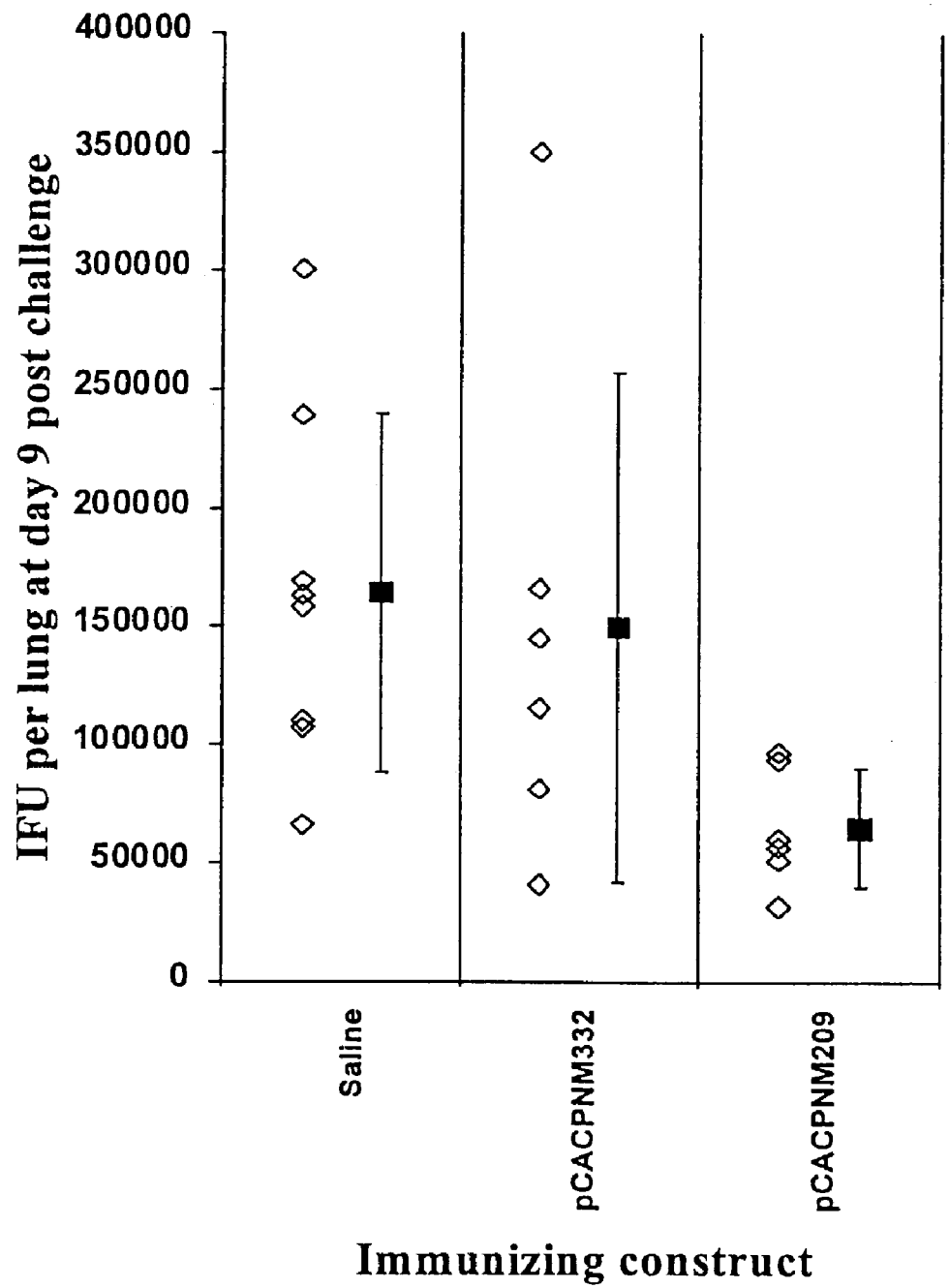

CHLAMYDIA ANTIGENS AND CORRESPONDING DNA FRAGMENTS AND USES THEREOF

REFERENCE TO RELATED APPLICATIONS

This is a continuation of U.S. patent application Ser. No. 09/824,567 filed Apr. 3, 2001 now abandoned which claims the benefit of U.S. Provisional Application No. 60/194,464, filed Apr. 4, 2000, the content of which is herein incorporated by reference.

FIELD OF INVENTION

The present invention relates to the *Chlamydia* ATP-binding cassette and corresponding DNA molecules, which can be used to prevent and treat *Chlamydia* infection in mammals, such as humans.

BACKGROUND OF THE INVENTION

*Chlamydiae* are prokaryotes. They exhibit morphologic and structural similarities to gram-negative bacteria including a trilaminar outer membrane, which contains lipopolysaccharide and several membrane proteins that are structurally and functionally analogous to proteins found in *E coli*. They are obligate intra-cellular parasites with a unique biphasic life cycle consisting of a metabolically inactive but infectious extracellular stage and a replicating but non-infectious intracellular stage. The replicative stage of the life-cycle takes place within a membrane-bound inclusion which sequesters the bacteria away from the cytoplasm of the infected host cell.

*C. pneumoniae* is a common human pathogen, originally described as the TWAR strain of *Chlamydia psittaci* but subsequently recognised to be a new species. *C. pneumoniae* is antigenically, genetically and morphologically distinct from other *chlamydia* species (*C. trachomatis, C. pecorum* and *C. psittaci*). It shows 10% or less DNA sequence homology with either of *C. trachomatis* or *C. psittaci*.

*C. pneumoniae* is the third most common cause of community acquired pneumonia, only less frequent than *Streptococcus pneumoniae* and *Mycoplasma pneumoniae* (Grayston et al. (1995) Journal of Infectious Diseases 168:1231; Campos et al. (1995) Investigation of Ophthalmology and Visual Science 36:1477). It can also cause upper respiratory tract symptoms and disease, including bronchitis and sinusitis (Grayston et al. (1995) Journal of Infectious Diseases 168:1231; Grayston et. al (1990) Journal of Infectious Diseases 161:618–625; Marrie (1993) Clinical Infectious Diseases. 18:501–513; Wang et al (1986) *Chlamydial* infections Cambridge University Press, Cambridge. p. 329. The great majority of the adult population (over 60%) has antibodies to *C. pneumoniae* (Wang et al (1986) *Chlamydial* infections. Cambridge University Press, Cambridge. p. 329), indicating past infection which was unrecognized or asymptomatic.

*C. pneumoniae* infection usually presents as an acute respiratory disease (i.e., cough, sore throat, hoarseness, and fever; abnormal chest sounds on auscultation). For most patients, the cough persists for 2 to 6 weeks; and recovery is slow. In approximately 10% of these cases, upper respiratory tract infection is followed by bronchitis or pneumonia. Furthermore, during a *C. pneumoniae* epidemic, subsequent co-infection with pneumococcus has been noted in about half of these pneumonia patients, particularly in the infirm and the elderly. As noted above, there is more and more evidence that *C. pneumoniae* infection is also linked to diseases other than respiratory infections.

The reservoir for the organism is presumably people. In contrast to *C. psittaci* infections, there is no known bird or animal reservoir. Transmission has not been clearly defined. It may result from direct contact with secretions, from fomites, or from airborne spread. There is a long incubation period, which may last for many months. Based on analysis of epidemics, *C. pneumoniae* appears to spread slowly through a population (case-to-case interval averaging 30 days) because infected persons are inefficient transmitters of the organism. Susceptibility to *C. pneumoniae* is universal. Reinfections occur during adulthood, following the primary infection as a child. *C. pneumoniae* appears to be an endemic disease throughout the world, noteworthy for superimposed intervals of increased incidence (epidemics) that persist for 2 to 3 years. *C. trachomatis* infection does not confer cross-immunity to *C. pneumoniae*. Infections are easily treated with oral antibiotics, tetracycline or erythromycin (2 g/d, for at least 10 to 14 d). A recently developed drug, azithromycin, is highly effective as a single-dose therapy against *chlamydial* infections.

In most instances, *C. pneumoniae* infection is often mild and without complications, and up to 90% of infections are subacute or unrecognized. Among children in industrialized countries, infections have been thought to be rare up to the age of 5 y, although a recent study (E Normann et al, *Chlamydia pneumoniae* in children with acute respiratory tract infections, Acta Paediatrica, 1998, Vol 87, Iss 1, pp 23–27) has reported that many children in this age group show PCR evidence of infection despite being seronegative, and estimates a prevalence of 17–19% in 2–4 y olds. In developing countries, the seroprevalence of *C. pneumoniae* antibodies among young children is elevated, and there are suspicions that *C. pneumoniae* may be an important cause of acute lower respiratory tract disease and mortality for infants and children in tropical regions of the world.

From seroprevalence studies and studies of local epidemics, the initial *C. pneumoniae* infection usually happens between the ages of 5 and 20 y. In the USA, for example, there are estimated to be 30,000 cases of childhood pneumonia each year caused by *C. pneumoniae*. Infections may cluster among groups of children or young adults.(e.g., school pupils or military conscripts).

*C. pneumoniae* causes 10 to 25% of community-acquired lower respiratory tract infections (as reported from Sweden, Italy, Finland, and the USA). During an epidemic, *C. pneumonia* infection may account for 50 to 60% of the cases of pneumonia. During these periods, also, more episodes of mixed infections with *S. pneumoniae* have been reported.

Reinfection during adulthood is common; the clinical presentation tends to be milder. Based on population seroprevalence studies, there tends to be increased exposure with age, which is particularly evident among men. Some investigators have speculated that a persistent, asymptomatic *C. pneumoniae* infection state is common.

In adults of middle age or older, *C. pneumoniae* infection may progress to chronic bronchitis and sinusitis. A study in the USA revealed that the incidence of pneumonia caused by *C. pneumoniae* in persons younger than 60 years is 1 case per 1,000 persons per year; but in the elderly, the disease incidence rose three-fold. *C. pneumoniae* infection rarely leads to hospitalization, except in patients with an underlying illness.

Of considerable importance is the association of atherosclerosis and *C. pneumoniae* infection. There are several epidemiological studies showing a correlation of previous infections with *C. pneumoniae* and heart attacks, coronary artery and carotid artery disease (Saikku et al.(1988) Lancet; ii:983–986; Thom et al. (1992) JAMA 268:68–72; Linnanmaki et al. (1993), Circulation 87:1030; Saikku et al. (1992) Annals Internal Medicine 116:273–287; Melnick et al (1993) American Journal of Medicine 95:499). Moreover, the organisms has been detected in atheromas and fatty streaks of the coronary, carotid, peripheral arteries and aorta (Shor et al. (1992) South African. Medical Journal 82:158–161; Kuo et al. (1993) Journal of Infectious Diseases 167:841–849; Kuo et al. (1993) Arteriosclerosis and Thrombosis 13:1501–1504; Campbell et al (1995) Journal of Infectious Diseases 172:585; Chiu et al. Circulation, 1997. Circulation. 96:2144–2148). Viable *C. pneumoniae* has been recovered from the coronary and carotid artery (Ramirez et al (1996) Annals of Internal Medicine 125: 979–982; Jackson et al. 1997. J. Infect. Dis. 176:292–295). Furthermore, it has been shown that *C. pneumoniae* can induce changes of atherosclerosis in a rabbit model (Fong et al. 1997. Journal of Clinical Microbiolology 35:48 and Laitinen et al. 1997. Infect. Immun. 65:4832–4835). Taken together, these results indicate that it is highly probable that *C. pneumoniae* can cause atherosclerosis in humans, though the epidemiological importance of *chlamydial* atherosclerosis remains to be demonstrated.

A number of recent studies have also indicated an association between *C. pneumoniae* infection and asthma. Infection has been linked to wheezing, asthmatic bronchitis, adult-onset asthma and acute exacerbations of asthma in adults, and small-scale studies have shown that prolonged antibiotic treatment was effective at greatly reducing the severity of the disease in some individuals (Hahn D L, et al. Evidence for *Chlamydia pneumoniae* infection in steroid-dependent asthma. Ann Allergy Asthma Immunol. 1998 Jan; 80(1): 45–49.; Hahn D L, et al. Association of *Chlamydia pneumoniae* IgA antibodies with recently symptomatic asthma. Epidemiol Infect. 1996 Dec; 117(3): 513–517; Bjornsson E, et al. Serology of *chlamydia* in relation to asthma and bronchial hyperresponsiveness. Scand J Infect Dis. 1996; 28(1): 63–69.; Hahn D L. Treatment of *Chlamydia pneumoniae* infection in adult asthma: a before-after trial. J Fam Pract. 1995 October; 41(4): 345–351.; Allegra L, et al. Acute exacerbations of asthma in adults: role of *Chlamydia pneumoniae* infection. Eur Respir J. 1994 December; 7(12): 2165–2168.; Hahn D L, et al. Association of *Chlamydia pneumoniae* (strain TWAR) infection with wheezing, asthmatic bronchitis, and adult-onset asthma. JAMA. 1991 Jul. 10; 266(2): 225–230).

In light of these results a protective vaccine against *C. pneumoniae* infection would be of considerable importance. There is not yet an effective vaccine for any human *chlamydial* infection. It is conceivable that an effective vaccine can be developed using physically or chemically inactivated *Chlamydiae*. However, such a vaccine does not have a high margin of safety. In general, safer vaccines are made by genetically manipulating the organism by attenuation or by recombinant means. Accordingly, a major obstacle in creating an effective and safe vaccine against human *chlamydial* infection has been the paucity of genetic information regarding *Chlamydia*, specifically *C. pneumoniae*.

Studies with *C. trachomatis* and *C. psittaci* indicate that safe and effective vaccine against *Chlamydia* is an attainable goal. For example, mice which have recovered from a lung infection with *C. trachomatis* are protected from infertility induced by a subsequent vaginal challenge (Pal et al. (1996) Infection and Immunity.64:5341). Similarly, sheep immunized with inactivated *C. psittaci* were protected from subsequent *chlamydial*-induced abortions and stillbirths (Jones et al. (1995) Vaccine 13:715). In a mouse model, protection from *chlamydial* infections has been associated with TH1 immune responses, particularly CD8+ CTL response (Rottenberg et al. 1999. J. Immunol. 162:2829–2836 and Penttila et al. 1999. Immunology. 97:490–496) and it is unlikely that similar responses will need to be induced in humans to confer protection. However, antigens able to elicit a protective immune response against *C. pneumoniae* are largely unknown. The presence of sufficiently high titres of neutralising antibody at mucosal surfaces can also exert a protective effect (Cotter et al. (1995) Infection and Immunity 63:4704).

Antigenic variation within the species *C. pneumoniae* is not well documented due to insufficient genetic information, though variation is expected to exist based on *C. trachomatis*. Serovars of *C. trachomatis* are defined on the basis of antigenic variation in the major outer membrane protein (MOMP), but published *C. pneumoniae* MOMP gene sequences show no variation between several diverse isolates of the organism (Campbell et al. Infection and Immunity (1990) 58:93;. McCafferty et al Infection and Immunity (1995) 63:2387–9; Gaydos et al. Infection and Immunity. (1992) 60(12):5319–5323). The gene encoding a 76 kDa antigen has been cloned from a single strain of *C. pneumoniae* and the sequence published (Perez Melgosa et al. Infection and Immunity. (1994) 62:880). An operon encoding the 9 kDa and 60 kDa cyteine-rich outer membrane protein genes has been described (Watson et al., Nucleic Acids Res (1990) 18:5299; Watson et al., Microbiology (1995) 141:2489). Many antigens recognized by immune sera to *C. pneumoniae* are conserved across all *chlamydiae*, but 98 kDa, 76 kDa and several other proteins may be *C. pneumoniae*-specific (Knudsen et al. Infect. Immun. 1999. 67:375–383; Perez Melgosa et al. Infection and Immunity. 1994. 62:880; Melgosa et al., FEMS Microbiol Lett 1993. 112:199;, Campbell et al., J. Clin. Microbiol. 1990. 28:1261; Iijima et al., J. Clin. Microbiol. 1994. 32:583). Antisera to 76 kDa and 54 kDa antigens have been reported to neutralize *C. pneumoniae* in vitro (Perez Melgosa et al. 1994. Infect. Immun. 62:880–886 and Wiedman-Al-Ahmad et al. 1997. Clin. Diagn. Lab. Immunol. 4:700–704). An assessment of the number and relative frequency of any *C. pneumoniae* serotypes, and the defining antigens, is not yet possible. The entire genome sequence of *C. pneumoniae* strain CWL-029 is now known (http://*chlamydia*-www.berkeley.edu:4231/) and as further sequences become available a better understanding of antigenic variation may be gained.

Many antigens recognised by immune sera to *C. pneumoniae* are conserved across all *chlamydiae*, but 98 kDa, 76 kDa and 54 kDa proteins appear to be *C. pneumoniae*-specific (Campos et al. (1995) Investigation of Ophthalmology and Visual Science 36:1477; Marrie (1993) Clinical Infectious Diseases. 18:501–513; Wiedmann-Al-Ahmad M, et al. Reactions of polyclonal and neutralizing anti-p54 monoclonal antibodies with an isolated, species-specific 54-kilodalton protein of *Chlamydia pneumoniae*. Clin Diagn Lab Immunol. 1997 November; 4(6): 700–704).

Immunoblotting of isolates with sera from patients does show variation of blotting patterns between isolates, indicating that serotypes *C. pneumoniae* may exist (Grayston et al. (1995) Journal of Infectious Diseases 168:1231; Ramirez et al (1996) Annals of Internal Medicine 125:979–982). However, the results are potentially confounded by the infection status of the patients, since immunoblot profiles of a patient's sera change with time post-infection. An assessment of the number and relative frequency of any serotypes, and the defining antigens, is not yet possible.

The use of DNA immunization to elicit a protective immune response in Balb/c mice against pulmonary infection with the mouse pneumonitis (MoPn) strain of *Chlamydia trachomatis* has recently been described (Zhang et al. 1997. J. Infect. Dis. 76:1035–1040 and Zhang et al. 1999. Immunology. 96:314–321). Recently the genome sequence from *C. pneumoniae* strain CM1 (ATCC #1360-VR) has been disclosed by Griffais in WO99/27105 on Jun. 3, 1999.

Accordingly, a need exists for identifying and isolating polynucleotide sequences of *C. pneumoniae* for use in preventing and treating *Chlamydia* infection.

SUMMARY OF THE INVENTION

The present invention provides purified and isolated polynucleotide molecules that encode the *Chlamydia* polypeptides designated ATP-binding cassette (SEQ ID No: 1) which can be used in methods to prevent, treat, and diagnose *Chlamydia* infection. In one form of the invention, the polynucleotide molecules are DNA that encode the polypeptide of SEQ ID No: 2.

Another form of the invention provides polypeptides corresponding to the isolated DNA molecules. The amino acid sequence of the corresponding encoded polypeptide is shown as SEQ ID No: 2.

Those skilled in the art will readily understand that the invention, having provided the polynucleotide sequences encoding the *Chlamydia* ATP-binding cassette, also provides polynucleotides encoding fragments derived from such a polypeptide. Moreover, the invention is understood to provide mutants and derivatives of such polypeptides and fragments derived therefrom, which result from the addition, deletion, or substitution of non-essential amino acids as described herein. Those skilled in the art would also readily understand that the invention, having provided the polynucleotide sequences encoding *Chlamydia* polypeptides, further provides monospecific antibodies that specifically bind to such polypeptides.

The present invention has wide application and includes expression cassettes, vectors, and cells transformed or transfected with the polynucleotides of the invention. Accordingly, the present invention further provides (i) a method for producing a polypeptide of the invention in a recombinant host system and related expression cassettes, vectors, and transformed or transfected cells; (ii) a vaccine, or a live vaccine vector such as a pox virus, *Salmonella typhimurium,* or *Vibrio cholerae* vector, containing a polypeptide or a polynucleotide of the invention, such vaccines and vaccine vectors being useful for, e.g., preventing and treating *Chlamydia* infection, in combination with a diluent or carrier, and related pharmaceutical compositions and associated therapeutic and/or prophylactic methods; (iii) a therapeutic and/or prophylactic use-of an RNA or DNA molecule of the invention, either in a naked form or formulated with a delivery vehicle, a polypeptide or combination of polypeptides, or a monospecific antibody of the invention, and related pharmaceutical compositions; (iv) a method for diagnosing the presence of *Chlamydia* in a biological sample, which can involve the use of a DNA or RNA molecule, a monospecific antibody, or a polypeptide of the invention; and (v) a method for purifying a polypeptide of the invention by antibody-based affinity chromatography.

BRIEF DESCRIPTION OF THE DRAWINGS

The present invention will be further understood from the following description with reference to-the drawings, in which:

FIG. 1 shows the nucleotide sequence of the ATP-binding cassette gene (SEQ ID No: 1) and the deduced amino acid sequence of the ATP-binding cassette from *Chlamydia pneumoniae* (SEQ ID No: 2).

FIG. 2 shows the restriction enzyme analysis of the *C. pneumoniae* ATP-binding cassette gene.

FIG. 4 illustrates protection against *C. pneumoniae* infection by pCACPNM209 following DNA immunization.

DETAILED DESCRIPTION OF INVENTION

Figure 3:
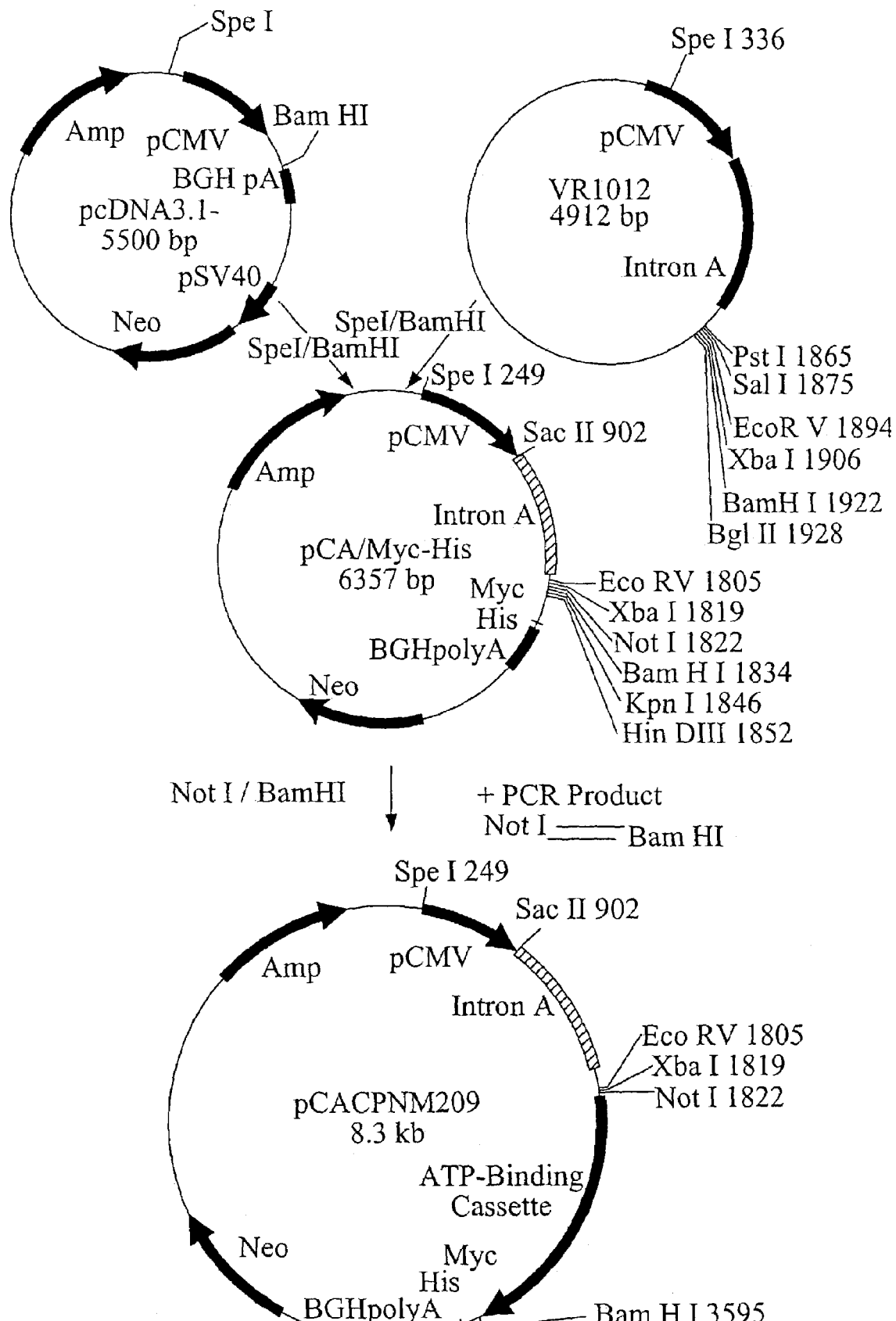
FIG. 3 shows the construction and elements of plasmid pCACPNM209.

An open reading frame (ORF) encoding the *Chlamydial* myosin ATP-binding cassette has been identified from the *C. pneumoniae* genome. The gene encoding this protein has been inserted into an expression plasmid and shown to confer immune protection against *chlamydial* infection. Accordingly, this ATP-binding cassette and related polypeptides can be used to prevent and treat *Chlamydia* infection.

According to a first aspect of the invention, isolated polynucleotides are provided which encode *Chlamydia* polypeptides, whose amino acid sequences are shown in SEQ ID No: 2.

The term "isolated polynucleotide" is defined as a polynucleotide removed from the environment in which it naturally occurs. For example, a naturally-occurring DNA molecule present in the genome of a living bacteria or as part of a gene bank is not isolated, but the same molecule separated from the remaining part of the bacterial genome, as a result of, e.g., a cloning event (amplification), is isolated. Typically, an isolated DNA molecule is free from DNA regions (e.g., coding regions) with which it is immediately contiguous at the 5' or 3' end, in the naturally occurring genome. Such isolated polynucleotides may be part of a vector or a composition and still be defined as isolated in that such a vector or composition is not part of the natural environment of such polynucleotide.

The polynucleotide of the invention is either RNA or DNA (cDNA, genomic DNA, or synthetic DNA), or modifications, variants, homologs or fragments thereof. The DNA is either double-stranded or single-stranded, and, if single-stranded, is either the coding strand or the non-coding (anti-sense) strand. Any one of the sequences that encode the polypeptides of the invention as shown in SEQ ID No: 1 is (a) a coding sequence, (b) a ribonucleotide sequence derived from transcription of (a), or (c) a coding sequence which uses the redundancy or degeneracy of the genetic code to encode the same polypeptides. By "polypeptide" or "protein" is meant any chain of amino acids, regardless of length or post-translational modification (e.g., glycosylation or phosphorylation). Both terms are used interchangeably in the present application.

Consistent with the first aspect of the invention, amino acid sequences are provided which are homologous to SEQ ID No: 2. As used herein, "homologous amino acid sequence" is any polypeptide which is encoded, in whole or in part, by a nucleic acid sequence which hybridizes at 25–35° C. below critical melting temperature (Tm), to any portion of the nucleic acid sequence of SEQ ID No: 1. A homologous amino acid sequence is one that differs from an amino acid sequence shown in SEQ ID No: 2 by one or more conservative amino acid substitutions. Such a sequence also encompass serotypic variants (defined below) as well as sequences containing deletions or insertions which retain inherent characteristics of the polypeptide such as immunogenicity. Preferably, such a sequence is at least 75%, more preferably 80%, and most preferably 90% identical to SEQ ID No: 2.

Homologous amino acid sequences include sequences that are identical or substantially identical to SEQ ID No: 2. By "amino acid sequence substantially identical" is meant a sequence that is at least 90%, preferably 95%, more preferably 97%, and most preferably 99% identical to an amino acid sequence of reference and that preferably differs from the sequence of reference by a majority of conservative amino acid substitutions.

Conservative amino acid substitutions are substitutions among amino acids of the same class. These classes include, for example, amino acids having uncharged polar side chains, such as asparagine, glutamine, serine, threonine, and tyrosine; amino acids having basic side chains, such as lysine, arginine, and histidine; amino acids having acidic side chains, such as aspartic acid and glutamic acid; and amino acids having nonpolar side chains, such as glycine, alanine, valine, leucine, isoleucine, praline, phenylalanine, methionine, tryptophan, and cysteine.

Homology is measured using sequence analysis software such as Sequence Analysis Software Package of the Genetics Computer Group, University of Wisconsin Biotechnology Center, 1710 University Avenue, Madison, Wis. 53705. Amino acid sequences are aligned to maximize identity. Gaps may be artificially introduced into the sequence to attain proper alignment. Once the optimal alignment has been set up, the degree of homology is established by recording all of the positions in which the amino acids of both sequences are identical, relative to the total number of positions.

Homologous polynucleotide sequences are defined in a similar way. Preferably, a homologous sequence is one that is at least 45%, more preferably 50%, 55%, 60%, 65%, 70%, 75%, 80%, and even more preferably 85%, 87%, 90%, 93%, 96% and most preferably 99% identical to the coding sequence of SEQ ID No: 1.

Consistent with the first aspect of the invention, polypeptides having a sequence homologous to SEQ ID No: 2 include naturally-occurring allelic variants, as well as mutants or any other non-naturally occurring variants that retain the inherent characteristics of the polypeptide of SEQ ID No: 2.

As is known in the art, an allelic variant is an alternate form of a polypeptide that is characterized as having a substitution, deletion, or addition of one or more amino acids that does not alter the biological function of the polypeptide. By "biological function" is meant the function of the polypeptide in the cells in which it naturally occurs, even if the function is not necessary for the growth or survival of the cells. For example, the biological function of a porin is to allow the entry into cells of compounds present in the extracellular medium. Biological function is distinct from antigenic property. A polypeptide can have more than one biological function.

Allelic variants are very common in nature. For example, a bacterial species such as *C. pneumoniae,* is usually represented by a variety of strains that differ from each other by minor allelic variations. Indeed, a polypeptide that fulfills the same biological function in different strains can have an amino acid sequence (and polynucleotide sequence) that is not identical in each of the strains. Despite this variation, an immune response directed generally against many allelic variants has been demonstrated. In studies of the *Chlamydial* MOMP antigen, cross-strain antibody binding plus neutralization of infectivity occurs despite amino acid sequence variation of MOMP from strain to strain, indicating that the MOMP, when used as an immunogen, is tolerant of amino acid variations.

Polynucleotides encoding homologous polypeptides or allelic variants are retrieved by polymerase chain reaction (PCR) amplification of genomic bacterial DNA extracted by conventional methods. This involves the use of synthetic oligonucleotide primers matching upstream and downstream of the 5' and 3' ends of the encoding domain. Suitable primers are designed according to the nucleotide sequence information provided in SEQ ID No: 1. The procedure is as follows: a primer is selected which consists of 10 to 40, preferably 15 to 25 nucleotides. It is advantageous to select primers containing C and G nucleotides in a proportion sufficient to ensure efficient hybridization; i.e., an amount of C and G nucleotides of at least 40%, preferably 50% of the total nucleotide content. A standard PCR reaction contains typically 0.5 to 5 Units of Taq DNA polymerase per 100 μL, 20 to 200 μM deoxynucleotide each, preferably at equivalent concentrations, 0.5 to 2.5 mM magnesium over the total deoxynucleotide concentration, $10^5$ to $10^6$ target molecules, and about 20 pmol of each primer. About 25 to 50 PCR cycles are performed, with an annealing temperature 15° C. to 5° C. below the true Tm of the primers. A more stringent annealing temperature improves discrimination against incorrectly annealed primers and reduces incorporation of incorrect nucleotides at the 3' end of primers. A denaturation temperature of 95° C. to 97° C. is typical, although higher temperatures may be appropriate for dematuration of G+C-rich targets. The number of-cycles performed depends on the starting concentration of target molecules, though typically more than 40 cycles is not recommended as non-specific background products tend to accumulate.

An alternative method for retrieving polynucleotides encoding homologous polypeptides or allelic variants is by hybridization screening of a DNA or RNA library. Hybridization procedures are well-known in the art and are described in Ausubel et al., (Ausubel et al., Current Protocols in Molecular Biology, John Wiley & Sons Inc., 1994), Silhavy et al. (Silhavy et al. Experiments with Gene Fusions, Cold Spring Harbor Laboratory Press, 1984), and Davis et al. (Davis et al. A Manual for Genetic Engineering: Advanced Bacterial Genetics, Cold Spring Harbor Laboratory Press, 1980)). Important parameters for optimizing hybridization conditions are reflected in a formula used to obtain the critical melting temperature above which two complementary DNA strands separate from each other (Casey & Davidson, Nucl. Acid Res. (1977) 4:1539). For polynucleotides of about 600 nucleotides or larger, this formula is as follows: Tm=81.5+0.41×(% G+C)+16.6 log (cation ion concentration)−0.63×(% formamide)−600/base number. Under appropriate stringency conditions, hybridization temperature (Th) is approximately 20 to 40° C., 20 to 25° C., or, preferably 30 to 40° C. below the calculated Tm. Those skilled in the art will understand that optimal temperature and salt conditions can be readily determined.

For the polynucleotides of the invention, stringent conditions are achieved for both pre-hybridizing and hybridizing incubations (i) within 4–16 hours at 42° C., in 6× SSC containing 50% formamide, or (ii) within 4–16 hours at 65° C. in an aqueous 6× SSC solution (1 M NaCl, 0.1 M sodium citrate (pH 7.0)). Typically, hybridization experiments are performed at a temperature from 60 to 68° C., e.g. 65° C. At such a temperature, stringent hybridization conditions can be achieved in 6× SSC, preferably in 2× SSC or 1× SSC, more preferably in 0.5× SSc, 0.3× SSC or 0.1× SSC (in the absence of formamide). 1× SSC contains 0.15 M NaCl and 0.015 M sodium citrate.

Useful homologs and fragments thereof that do not occur naturally are designed using known methods for identifying regions of an antigen that are likely to tolerate amino acid sequence changes and/or deletions. As an example, homologous polypeptides from different species are compared; conserved sequences are identified. The more divergent sequences are the most likely to tolerate sequence changes. Homology among sequences may be analyzed using, as an example, the BLAST homology searching algorithm of Altschul et al., Nucleic Acids Res.; 25:3389–3402 (1997). Alternatively, sequences are modified such that they become more reactive to T- and/or B-cells, based on computer-assisted analysis of probable T- or B-cell epitopes. Yet another alternative is to mutate a particular amino acid residue or sequence within the polypeptide in vitro, then screen the mutant polypeptides for their ability to prevent or treat Chlamydia infection according to the method outlined below.

A person skilled in the art will readily understand that by following the screening process of this invention, it will be determined without undue experimentation whether a particular homolog of SEQ ID No. 2 may be useful in the prevention or treatment of Chlamydia infection. The screening procedure comprises the steps:

(i) immunizing an animal, preferably mouse, with the test homolog or fragment;

(ii) inoculating the immunized animal with Chlamydia; and (iii) selecting those homologs or fragments which confer protection against Chlamydia.

By "conferring protection" is meant that there is a reduction in severity of any of the effects of Chlamydia infection, in comparison with a control animal which was not immunized with the test homolog or fragment.

Consistent with the first aspect of the invention, polypeptide derivatives are provided that are partial sequences of SEQ ID No. 2, partial sequences of polypeptide sequences homologous to SEQ ID No. 2, polypeptides derived from full-length polypeptides by internal deletion, and fusion proteins.

It is an accepted practice in the field of immunology to use fragments and variants of protein immunogens as vaccines, as all that is required to induce an immune response to a protein is a small (e.g., 8 to 10 amino acid) immunogenic region of the protein. Various short synthetic peptides corresponding to surface-exposed antigens of pathogens other than Chlamydia have been shown to be effective vaccine antigens against their respective pathogens, e.g. an 11 residue peptide of murine mammary tumor virus (Casey & Davidson, Nucl. Acid Res. (1977) 4:1539), a 16-residue peptide of Semliki Forest virus (Snijders et al., 1991. J. Gen. Virol. 72:557–565), and two overlapping peptides of 15 residues each from canine parvovirus (Langeveld et al., Vaccine 12(15):1473–1480, 1994).

Accordingly, it will be readily apparent to one skilled in the art, having read the present description, that partial sequences of SEQ ID No. 2 or their homologous amino acid sequences are inherent to the full-length sequences and are taught by the present invention. Such polypeptide fragments preferably are at least 12 amino acids in length. Advantageously, they are at least 15 amino acids, preferably at least 20, 25, 30, 35, 40, 45, 50 amino acids, more preferably at least 55, 60, 65, 70, 75 amino acids, and most preferably at least 80, 85, 90, 95, 100 amino acids in length.

Polynucleotides of 30 to 600 nucleotides encoding partial sequences of sequences homologous to SEQ ID No: 2 are retrieved by PCR amplification using the parameters outlined above and using primers matching the sequences upstream and downstream of the 5' and 3' ends of the fragment to be amplified. The template polynucleotide for such amplification is either the full length polynucleotide homologous to SEQ ID No: 1, or a polynucleotide contained in a mixture of polynucleotides such as a DNA or RNA library. As an alternative method for retrieving the partial sequences, screening hybridization is carried out under conditions described above and using the formula for calculating Tm. Where fragments of 30 to 600 nucleotides are to be retrieved, the calculated Tm is corrected by subtracting (600/polynucleotide size in base pairs) and the stringency conditions are defined by a hybridization temperature that is 5 to 10° C. below Tm. Where oligonucleotides shorter than 20–30 bases are to be obtained, the formula for calculating the Tm is as follows: $Tm=4\times(G+C)+2(A+T)$. For example, an 18 nucleotide fragment of 50% G+C would have an approximate Tm of 54° C. Short peptides that are fragments of SEQ ID No: 2 or its homologous sequences, are obtained directly by chemical synthesis (E. Gross and H. J. Meinhofer, 4 The Peptides: Analysis, Synthesis, Biology; Modern Techniques of Peptide Synthesis, John Wiley & Sons (1981), and M. Bodanzki, Principles of Peptide Synthesis, Springer-Verlag (1984)).

Useful polypeptide derivatives, e.g., polypeptide fragments, are designed using computer-assisted analysis of amino acid sequences. This would identify probable surface-exposed, antigenic regions (Hughes et al., 1992. Infect. Immun. 60(9):3497). Analysis of 6 amino acid sequences contained in SEQ ID No: 2, based on the product of flexibility and hydrophobicity propensities using the program SEQSEE (Wishart D S, et al. "SEQSEE: a comprehensive program suite for protein sequence analysis." Comput Appl Biosci. 1994 Apr;10(2):121–32), can reveal potential B- and T-cell epitopes which may be used as a basis for selecting useful immunogenic fragments and variants. This analysis uses a reasonable combination of external surface features that is likely to be recognized by antibodies. Probable T-cell epitopes for HLA-A0201 MHC subclass may be revealed by an algorithms that emulate an approach developed at the NIH (Parker K C, et al. "Peptide binding to MHC class I molecules: implications for antigenic peptide prediction." Immunol Res 1995;14(1):34–57).

Epitopes which induce a protective T cell-dependent immune response are present throughout the length of the polypeptide. However, some epitopes may be masked by secondary and tertiary structures of the polypeptide. To reveal such masked epitopes large internal deletions are created which remove much of the original protein structure and exposes the masked epitopes. Such internal deletions sometimes effect the additional advantage of removing immunodominant regions of high variability among strains.

Polynucleotides encoding polypeptide fragments and polypeptides having large internal deletions are constructed using standard methods (Ausubel et al., Current Protocols in Molecular Biology, John Wiley & Sons Inc., 1994). Such methods include standard PCR, inverse PCR, restriction enzyme treatment of cloned DNA molecules, or the method of Kunkel et al. (Kunkel et al. Proc. Natl. Acad. Sci. USA (1985) 82:448). Components for these methods and instructions for their use are readily available from various commercial sources such as Stratagene. Once the deletion mutants have been constructed, they are tested for their ability to prevent or treat *Chlamydia* infection as described above.

As used herein, a fusion polypeptide is one that contains a polypeptide or a polypeptide derivative of the invention fused at the N- or C-terminal end to any other polypeptide (hereinafter referred to as a peptide tail). A simple way to obtain such a fusion polypeptide is by translation of an in-frame fusion of the polynucleotide sequences, i.e., a hybrid gene. The hybrid gene encoding the fusion polypeptide is inserted into an expression vector which is used to transform or transfect a host cell. Alternatively, the polynucleotide sequence encoding the polypeptide or polypeptide derivative is inserted into an expression vector in which the polynucleotide encoding the peptide tail is already present. Such vectors and instructions for their use are commercially available, e.g. the pMal-c2 or pMal-p2 system from New England Biolabs, in which the peptide tail is a maltose binding protein, the glutathione-S-transferase system of Pharmacia, or the His-Tag system available from Novagen. These and other expression systems provide convenient-means for further purification of polypeptides and derivatives of the invention.

An advantageous example of a fusion polypeptide is one where the polypeptide or homolog or fragment of the invention is fused to a polypeptide having adjuvant activity, such as subunit B of either cholera toxin or *E. coli* heat-labile toxin. Another advantageous fusion is one where the polypeptide, homolog or fragment is fused to a strong T-cell epitope or B-cell epitope. Such an epitope may be one known in the art (e.g. the Hepatitis B virus core antigen, D. R. Millich et al., "Antibody production to the nucleocapsid and envelope of the Hepatitis B virus primed by a single synthetic T cell site", Nature. 1987. 329:547–549), or one which has been identified in another polypeptide of-the invention based on computer-assisted analysis of probable T- or B-cell epitopes. Consistent with this aspect of the invention is a fusion polypeptide comprising T- or B-cell epitopes from SEQ ID No: 2 or its homolog or fragment, wherein the epitopes are derived from multiple variants of said polypeptide or homolog or fragment, each variant differing from another in the location and sequence of its epitope within the polypeptide. Such a fusion is effective in the prevention and treatment of *Chlamydia* infection since it optimizes the T- and B-cell response to the overall polypeptide, homolog or fragment.

To effect fusion, the polypeptide of the invention is fused to the N-, or preferably, to the C-terminal end of the polypeptide having adjuvant activity or T- or B-cell epitope. Alternatively, a polypeptide fragment of the invention is inserted internally within the amino acid sequence of the polypeptide having adjuvant activity. The T- or B-cell epitope may also be inserted internally within the amino acid sequence of the polypeptide of the invention.

Consistent with the first aspect, the polynucleotides of the invention also encode hybrid precursor polypeptides containing heterologous signal peptides, which mature into polypeptides of the invention. By "heterologous signal peptide" is meant a signal peptide that is not found in naturally-occurring precursors of polypeptides of the invention.

Polynucleotide molecules according to the invention, including RNA, DNA, or modifications or combinations thereof, have various applications. A DNA molecule is used, for example, (i) in a process for producing the encoded polypeptide in a recombinant host system, (ii) in the construction of vaccine vectors such as poxviruses, which are further used in methods and compositions for preventing and/or treating *Chlamydia* infection, (iii) as a vaccine agent (as well as an RNA molecule), in a naked form or formulated with a delivery vehicle and, (iv) in the construction of attenuated *Chlamydia* strains that can over-express a polynucleotide of the invention or express it in a non-toxic, mutated form.

Accordingly, a second aspect of the invention encompasses (i) an expression cassette containing a DNA molecule of the invention placed under the control of the elements required for expression, in particular under the control of an appropriate promoter; (ii) an expression vector containing an expression cassette of the invention; (iii) a procaryotic or eucaryotic cell transformed or transfected with an expression cassette and/or vector of the invention, as well as (iv) a process for producing a polypeptide or polypeptide derivative encoded by a polynucleotide of the invention, which involves culturing a procaryotic or eucaryotic cell transformed or transfected with an expression cassette and/or vector of the invention, under conditions that allow expression of the DNA molecule of the invention and, recovering the encoded polypeptide or polypeptide derivative from the cell culture.

A recombinant expression system is selected from procaryotic and eucaryotic hosts. Eucaryotic hosts include yeast cells (e.g., *Saccharomyces cerevisiae* or *Pichia' pastoris*), mammalian cells (e.g., COS1, NIH3T3, or JEG3 cells), arthropods cells (e.g., *Spodoptera frugiperda* (SF9) cells), and plant cells. A preferred expression system is a procaryotic host such as *E. coli.* Bacterial and eucaryotic cells are available from a number of different sources including commercial sources to those skilled in the art, e.g., the American Type Culture Collection (ATCC; Rockville, Md.). Commercial sources of cells used for recombinant protein expression also provide instructions for usage of the cells.

The choice of the expression system depends on the features desired for the expressed polypeptide. For example, it may be useful to produce a polypeptide of the invention in a particular lipidated form or any other form.

One skilled in the art would redily understand that not all vectors and expression control sequences and hosts would be expected to express equally well the polynucleotides of this invention. With the guidelines described below, however, a selection of vectors, expression control sequences and hosts may be made without undue experimentation and without departing from the scope of this invention.

In selecting a vector, the host must be chosen that is compatible with the vector which is to exist and possibly replicate in it. Considerations are made with respect to the vector copy number, the ability to control the copy number, expression of other proteins such as antibiotic resistance. In selecting an expression control sequence, a number of variables are considered. Among the important variable are the relative strength of the sequence (e.g. the ability to drive expression under various conditions), the ability to control the sequence's function, compatibility between the polynucleotide to be expressed and the control sequence (e.g. secondary structures are considered to avoid hairpin structures which prevent efficient transcription). In selecting the host, unicellular hosts are selected which are compatible with the selected vector, tolerant of any possible toxic effects of the expressed product, able to secrete the expressed product efficiently if such is desired, to be able to express the product in the desired conformation, to be easily scaled up, and to which ease of purification of the final product.

The choice of the expression cassette depends on the host system selected as well as the features desired for the expressed polypeptide. Typically, an expression cassette includes a promoter that is functional in the selected host system and can be constitutive or inducible; a ribosome binding site; a start codon (ATG) if necessary; a region encoding a signal peptide, e.g., a lipidation signal peptide; a DNA molecule of the invention; a stop codon; and optionally a 3' terminal region (translation and/or transcription terminator). The signal peptide encoding region is adjacent to the polynucleotide of the invention and placed in proper reading frame. The signal peptide-encoding region is homologous or heterologous to the DNA molecule encoding the mature polypeptide and is compatible with the secretion apparatus of the host used for expression. The open reading frame constituted by the DNA molecule of the invention, solely or together with the signal peptide, is placed under the control of the promoter so that transcription and translation occur in the host system. Promoters and signal peptide encoding regions are widely known and available to those skilled in the art and include, for example, the promoter of *Salmonella typhimurium* (and derivatives) that is inducible by arabinose (promoter araB) and is functional in Gram-negative bacteria such as *E. coli* (as described in U.S. Pat. No. 5,028,530 and in Cagnon et al., (Cagnon et al., Protein Engineering (1991) 4(7):843)); the promoter of the gene of bacteriophage T7 encoding RNA polymerase, that is functional in a number of *E. coli* strains expressing T7 polymerase (described in U.S. Pat. No. 4,952,496); OspA lipidation signal peptide; and RlpB lipidation signal peptide (Takase et al., J. Bact. (1987) 169:5692).

The expression cassette is typically part of an expression vector, which is selected for its ability to replicate in the chosen expression system. Expression vectors (e.g., plasmids or viral vectors) can be chosen, for example, from those described in Pouwels et al. (Cloning Vectors: A Laboratory Manual 1985, Supp. 1987). Suitable expression vectors can be purchased from various commercial sources.

Methods for transforming/transfecting host cells with expression vectors are well-known in the art and depend on the host system selected as described in Ausubel et al., (Ausubel et al., Current Protocols in Molecular Biology, John Wiley & Sons Inc., 1994).

Upon expression, a recombinant polypeptide of the invention (or a polypeptide derivative) is produced and remains in the intracellular compartment, is secreted/excreted in the extracellular medium or in the periplasmic space, or is embedded in the cellular membrane. The polypeptide is recovered in a substantially purified form from the cell extract or from the supernatant after centrifugation of the recombinant cell culture. Typically, the recombinant polypeptide is purified by antibody-based affinity purification or by other well-known methods that can be readily adapted by a person skilled in the art, such as fusion of the polynucleotide encoding the polypeptide or its derivative to a small affinity binding domain. Antibodies useful for purifying by immunoaffinity the polypeptides of the invention are obtained as described below.

A polynucleotide of the invention can also be useful as a vaccine. There are two major routes, either using a viral or bacterial host as gene delivery vehicle (live vaccine vector) or administering the gene in a free form, e.g., inserted into a plasmid. Therapeutic or prophylactic efficacy of a polynucleotide of the invention is evaluated as described below.

Accordingly, a third aspect of the invention provides (i) a vaccine vector such as a poxvirus, containing a DNA molecule of the invention, placed under the control of elements required for expression; (ii) a composition of matter comprising a vaccine vector of the invention, together with a diluent or carrier; specifically (iii) a pharmaceutical composition containing a therapeutically or prophylactically effective amount of a vaccine vector of the invention; (iv) a method for inducing an immune response against *Chlamydia* in a mammal (e.g., a human; alternatively, the method can be used in veterinary applications for treating or preventing *Chlamydia* infection of animals, e.g., cats or birds), which involves administering to the mammal an immunogenically effective amount of a vaccine vector of the invention to elicit a protective or therapeutic immune response to *Chlamydia*; and particularly, (v) a method for preventing and/or treating a *Chlamydia* (e.g., *C. trachomatis, C. psittaci, C. pneumonia, C. pecorum*) infection, which involves administering a prophylactic or therapeutic amount of a vaccine vector of the invention to an infected individual. Additionally, the third aspect of the invention encompasses the use of a vaccine vector of the invention in the preparation of a medicament for preventing and/or treating *Chlamydia* infection.

As used herein, a vaccine vector expresses one or several polypeptides or derivatives of the invention. The vaccine vector may express additionally a cytokine, such as interleukin-2 (IL-2) or interleukin-12 (IL-12), that enhances the immune response (adjuvant effect). It is understood that each of the components to be expressed is placed under the control of elements required for expression in a mammalian cell.

Consistent with the third aspect of the invention is a composition comprising several vaccine vectors, each of them capable of expressing a polypeptide or derivative of the invention. A composition may also comprise a vaccine vector capable of expressing an additional *Chlamydia* antigen, or a subunit, fragment, homolog, mutant, or derivative thereof; optionally together with or a cytokine such as IL-2 or IL-12.

A general principle is that recognition of a particular antigen is not in itself sufficient to produce an effective immune response. In some cases, a cell-mediated response is appropriate; in others, antibody.

Antigens of microorganisms vary considerably in their accessibility to cells of the immune system. Antigens which normally occur inside a pathogen may become accessible only when the pathogen or an infected cell is killed. Even antigens expressed at the cell surface may present only a limited range of their potential epitopes for antibody binding, depending on their orientation in the membrane. Protective structures, such as bacterial capsules, further limit the effective recognition of epitopes.

A distinction should be drawn between the overall composition of the immune response, those components of it which are important in the resolution of infection and the components which are responsible for the prevention of re-infection. In many cases, particular elements of the immune response are critically important; for example, cell-mediated immunity in leprosy. Even when considering a particular effector system, the response directed against some antigens is often much more effective than the responses to others. Immune responses to particular microbial antigens have different degrees of relevance to anti-microbial immunity, depending on the nature of the organism, it pathogenicity and the nature of the immune response it initiates.

The primary effectors against extracellular pathogens are antibody and complement. Binding of antibody to receptors on the pathogen can prevent it from attaching to its target cell. Antibody alone, or more effectively in association with complement, opsonizes pathogens for uptake by phagocytes expressing Fc receptors and complement receptors CR1 and CR3. Usually this will lead to intracellular destruction of the pathogen but if the phagocyte is unable to destroy it and is a facultative host cell, then antibody may actually promote the spread of infection. Such an eventuality, however, depends on the dynamic balance between the actions of the humoral and cell-mediated immune responses.

Sometimes effective antibodies must be of the right class to activate appropriate effectors. The important antigens are those involved in evasion of immune effector mechanisms; that is, pili, fimbriae and capsular antigens which constitute the major antigens of the outer layer of bacteria. Often epitope specificity is important, since it determines whether complement is deposited in a position to damage the outer membrane. There are also numerous protein antigens which can induce an antibody response; however, although the antibody response is partly species-specific and may be diagnostically useful, it is largely irrelevant to immunity. This is most obvious in lepromatous leprosy, where the patients have weak cell-mediated immunity, high levels of specific antibody and tissues heavily infected with bacteria.

In some cases, a particular type of antibody response is mandatory for clearance of the pathogen. This is true of many bacterial infections, where specific antibodies to surface antigens are necessary to neutralize the bacterial defences and opsonize the bacteria for phagocytes.

There are also cases where responses to individual antigens are essential for host immunity. The simplest examples are the toxins produced by the causative agents of diphtheria, tetanus and clostridial enteritis. The damage produced directly by the infectious agent in these diseases is slight by comparison with that produced by the secreted toxins. Consequently, protection against these conditions involves immunization to toxoids. Nevertheless, the immune system must still eradicate the primary site of the bacterial infection if the disease is to be resolved. The target antigens for bactericidal antibodies are extremely diverse and include LPS, capsular polysaccharides and other outer membrane proteins. Virulence factors can also provide good immunogens in a vaccine.

Vaccination methods for treating or preventing infection in a mammal comprises use of a vaccine vector of the invention to be administered by any conventional route, particularly to a mucosal (e.g., ocular, intranasal, oral, gastric, pulmonary, intestinal, rectal, vaginal, or urinary tract) surface or via the parenteral (e.g., subcutaneous, intradermal, intramuscular, intravenous, or intraperitoneal) route. Preferred routes depend upon the choice of the vaccine vector. Treatment may be effected in a single dose or repeated at intervals. The appropriate-dosage depends on various parameters understood by skilled artisans such as the vaccine vector itself, the route of administration or the condition of the mammal to be vaccinated (weight, age and the like).

Live vaccine vectors available in the art include viral vectors such as adenoviruses and poxviruses as well as bacterial vectors, e.g., *Shigella, Salmonella, Vibrio cholerae, Lactobacillus,* Bacille bilié de Calmette-Guérin (BCG), and *Streptococcus.*

An example of an adenovirus vector, as well as a method for constructing an adenovirus vector capable of expressing a DNA molecule of the invention, are described in U.S. Pat. No. 4,920,209. Poxvirus vectors include vaccinia and canary pox virus, described in U.S. Pat. No. 4,722,848 and U.S. Pat. No. 5,364,773, respectively. (Also see, e.g., Tartaglia et al., Virology (1992) 188:217) for a description of a vaccinia virus vector and Taylor et al, Vaccine (1995) 13:539 for a reference of a canary pox.) Poxvirus vectors capable of expressing a polynucleotide of the invention are obtained by homologous recombination as described in Kieny et al., Nature (1984) 312:163 so that the polynucleotide of the invention is inserted in the viral genome under appropriate conditions for expression in mammalian cells. Generally, the dose of vaccine viral vector, for therapeutic or prophylactic use, can be of from about $1\times10^4$ to about $1\times10^{11}$, advantageously from about $1\times10^7$ to about $1\times10^{10}$, preferably of from about $1\times10^7$ to about $1\times10^9$ plaque-forming units per kilogram. Preferably, viral vectors are administered parenterally; for example, in 3 doses, 4 weeks apart. It is preferable to avoid adding a chemical adjuvant to a composition containing a viral vector of the invention and thereby minimizing the immune response to the viral vector itself.

Non-toxicogenic *Vibrio cholerae* mutant strains that are useful as a live oral vaccine are known. Mekalanos et al., Nature (1983) 306:551 and U.S. Pat. No. 4,882,278 describe strains which have a substantial amount of the coding sequence of each of the two ctxA alleles deleted so that no functional cholerae toxin is produced. WO 92/11354 describes a strain in which the irgA locus is inactivated by mutation; this mutation can be combined in a single strain with ctxA mutations. WO 94/01533 describes a deletion mutant lacking functional ctxA and attRS1 DNA sequences. These mutant strains are genetically engineered to express heterologous antigens, as described in WO 94/19482. An effective vaccine dose of a *Vibrio cholerae* strain capable of expressing a polypeptide or polypeptide derivative encoded by a DNA molecule of the invention contains about $1\times10^5$ to about $1\times10^9$, preferably about $1\times10^6$ to about $1\times10^8$, viable bacteria in a volume appropriate for the selected route of administration. Preferred routes of administration include all mucosal routes; most preferably, these vectors are administered intranasally or orally.

Attenuated *Salmonella typhimurium* strains, genetically engineered for recombinant expression of heterologous antigens or not, and their use as oral vaccines are described in Nakayama et al. (Bio/Technology (1988) 6:693) and WO 92/11361. Preferred routes of administration include all mucosal routes; most preferably, these vectors are administered intranasally or orally.

Other bacterial strains used as vaccine vectors in the context of the present invention are described for *Shigella flexneri* in High et al., EMBO (1992) 11:1991 and Sizemore et al., Science (1995) 270:299; for *Streptococcus gordonii* in Medaglini et al., Proc. Natl. Acad. Sci. USA (1995) 92:6868; and for Bacille Calmette Guerin in Flynn J. L., Cell. Mol. Biol. (1994) 40 (suppl. I):31, WO 88/06626, WO 90/00594, WO 91/13157, WO 92/01796, and WO 92/21376.

In bacterial vectors, the polynucleotide of the invention is inserted into the bacterial genome or remains in a free state as part of a plasmid.

The composition comprising a vaccine bacterial vector of the present invention may further contain an adjuvant. A number of adjuvants are known to those skilled in the art. Preferred adjuvants are selected as provided below.

Accordingly, a fourth aspect of the invention provides (i) a composition of matter comprising a polynucleotide of the invention, together with a diluent or carrier; (ii) a pharmaceutical composition comprising a therapeutically or prophylactically effective amount of a polynucleotide of the invention; (iii) a method for inducing an immune response against *Chlamydia* in a mammal by administration of an immunogenically effective amount of a polynucleotide of the invention to elicit a protective immune response to *Chlamydia*; and particularly, (iv) a method for preventing and/or treating a *Chlamydia* (e.g., *C. trachomatis, C. psit-*

*taci, C. pneumoniae,* or *C. pecorum*) infection, by administering a prophylactic or therapeutic amount of a polynucleotide of the invention to an infected individual. Additionally, the fourth aspect of the invention encompasses the use of a polynucleotide of the invention in the preparation of a medicament for preventing and/or treating *Chlamydia* infection. A preferred use includes the use of a DNA molecule placed under conditions for expression in a mammalian cell, especially in a plasmid that is unable to replicate in mammalian cells and to substantially integrate in a mammalian genome.

Use of the polynucleotides of the invention include their administration to a mammal as a vaccine, for therapeutic or prophylactic purposes. Such polynucleotides are used in the form of DNA as part of a plasmid that is unable to replicate in a mammalian cell and unable to integrate into the mammalian genome. Typically, such a DNA molecule is placed under the control of a promoter suitable for expression in a mammalian cell. The promoter functions either ubiquitously or tissue-specifically. Examples of non-tissue specific promoters include the early Cytomegalovirus (CMV) promoter (described in U.S. Pat. No. 4,168,062) and the Rous Sarcoma Virus promoter (described in Norton & Coffin, Molec. Cell Biol. (1985) 5:281). An example of a tissue-specific promoter is the desmin promoter which drives expression in muscle cells (Li et al., Gene (1989) 78:243, Li & Paulin, J. Biol. Chem. (1991) 266:6562 and Li & Paulin, J. Biol. Chem. (1993) 268:10403). Use of promoters is well-known to those skilled in the art. Useful vectors are described in numerous publications, specifically WO 94/21797 and Hartikka et al., Human Gene Therapy (1996) 7:1205.

Polynucleotides of the invention which are used as vaccines encode either a precursor or a mature form of the corresponding polypeptide. In the precursor form, the signal peptide is either homologous or heterologous. In the latter case, a eucaryotic leader sequence such as the leader sequence of the tissue-type plasminogen factor (tPA) is preferred.

As used herein, a composition of the invention contains one or several polynucleotides with optionally at least one additional-polynucleotide encoding another *Chlamydia* antigen such as urease subunit A, B. or both, or a fragment, derivative, mutant, or analog thereof. The composition may also contain an additional polynucleotide encoding a cytokine, such as interleukin-2 (IL-2) or interleukin-12 (IL-12) so that the immune response is enhanced. These additional polynucleotides are placed under appropriate control for expression. Advantageously, DNA molecules of the invention and/or additional DNA molecules to be included in the same composition, are present in the same plasmid.

Standard techniques of molecular biology for preparing and purifying polynucleotides are used in the preparation of polynucleotide therapeutics of the invention. For use as a vaccine, a polynucleotide of the invention is formulated according to various methods outlined below.

One method utilizizes the polynucleotide in a naked form, free of any delivery vehicles. Such a polynucleotide is simply diluted in a physiologically acceptable solution such as sterile saline or sterile buffered saline, with or without a carrier. When present, the carrier preferably is isotonic, hypotonic, or weakly hypertonic, and has a relatively low ionic strength, such as provided by a sucrose solution, e.g., a solution containing 20% sucrose.

An alternative method utilizes the polynucleotide in association with agents that assist in cellular uptake. Examples of such agents are (i) chemicals that modify cellular permeability, such as bupivacaine (see, e.g., WO 94/16737), (ii) liposomes for encapsulation of the polynucleotide, or (iii) cationic lipids or silica, gold, or tungsten microparticles which associate themselves with the polynucleotides.

Anionic and neutral liposomes are well-known in the art (see, e.g., Liposomes: A Practical Approach, RPC New Ed, IRL press (1990), for a detailed description of methods for making liposomes) and are useful for delivering a large range of products, including polynucleotides.

Cationic lipids are also known in the art and are commonly used for gene delivery. Such lipids include Lipofectin™ also known as DOTMA (N-[1-(2,3-dioleyloxy)propyl]-N,N,N-trimethylammonium chloride), DOTAP (1,2-bis (oleyloxy)-3-(trimethylammonio)propane), DDAB (dimethyldioctadecylammonium bromide), DOGS (dioctadecylamidologlycyl spermine) and cholesterol derivatives such as DC-Chol (3 beta-(N-(N',N'-dimethyl aminomethane)-carbamoyl) cholesterol). A description of these cationic lipids can be found in EP 187,702, WO 90/11092, U.S. Pat. No. 5,283,185, WO 91/15501, WO 95/26356, and U.S. Pat. No. 5,527,928. Cationic lipids for gene delivery are preferably used in association with a neutral lipid such as DOPE (dioleyl phosphatidylethanolamine), as described in WO 90/11092 as an example.

Formulation containing cationic liposomes may optionally contain other transfection-facilitating compounds. A number of them are described in WO 93/18759, WO 93/19768, WO 94/25608, and WO 95/02397. They include spermine derivatives useful for facilitating the transport of DNA through the nuclear membrane (see, for example, WO 93/18759) and membrane-permeabilizing compounds such as GALA, Gramicidine S, and cationic bile salts (see, for example, WO 93/19768).

Gold or tungsten microparticles are used for gene delivery, as described in WO 91/00359, WO 93/17706, and Tang et al. Nature (1992) 356:152. The microparticle-coated polynucleotide is injected via intradermal or intraepidermal routes using a needleless injection device ("gene gun"), such as those described in U.S. Pat. No. 4,945,050, U.S. Pat. No. 5,015,580, and WO 94/24263.

The amount of DNA to-be used in a vaccine recipient depends, e.g., on the strength of the promoter used in the DNA construct, the immunogenicity of the expressed gene product, the condition of the mammal intended for administration (e.g., the weight, age, and general health of the mammal), the mode of administration, and the type of formulation. In general, a therapeutically or prophylactically effective dose from about 1 µg to about 1 mg, preferably, from about 10 µg to about 800 µg and, more preferably, from about 25 µg to about 250 µg, can be administered to human adults. The administration can be achieved in a single dose or repeated at intervals.

The route of administration is any conventional route used in the vaccine field. As general guidance, a polynucleotide of the invention is administered via a mucosal surface, e.g., an ocular, intranasal, pulmonary, oral, intestinal, rectal, vaginal, and urinary tract surface; or via a parenteral route, e.g., by an intravenous, subcutaneous, intraperitoneal, intradermal, intraepidermal, or intramuscular route. The choice of administration route depends on the formulation that is selected. A polynucleotide formulated in association with bupivacaine is advantageously administered into muscles. When a neutral or anionic liposome or a cationic lipid, such as DOTMA or DC-Chol, is used, the formulation can be advantageously injected via intravenous, intranasal (aerosolization), intramuscular, intradermal, and subcutaneous routes. A polynucleotide in a naked form can advantageously be administered via the intramuscular, intradermal, or sub-cutaneous routes.

Although not absolutely required, such a composition can also contain an adjuvant. If so, a systemic adjuvant that does not require concomitant administration in order to exhibit an adjuvant effect is preferable such as, e.g., QS21, which is described in U.S. Pat. No. 5,057,546.

The sequence information provided in the present application enables the design of specific nucleotide probes and primers that are used for diagnostic purposes. Accordingly, a fifth aspect of the invention provides a nucleotide probe or primer having a sequence found in or derived by degeneracy of the genetic code from a sequence shown in SEQ ID No: 1.

The term "probe" as used in the present application refers to DNA (preferably single stranded) or RNA molecules (or modifications or combinations thereof) that hybridize under the stringent conditions, as defined above, to nucleic acid molecules having SEQ ID No: 1 or to sequences homologous to SEQ ID No: 1, or to its complementary or anti-sense sequence. Generally, probes are significantly shorter than full-length sequences. Such probes contain from about 5 to about 100, preferably from about 10 to about 80, nucleotides. In particular, probes have sequences that are at least 75%, preferably at least 85%, more preferably 95% homologous to a portion of SEQ ID No: 1 or that are complementary to such sequences. Probes may contain modified bases such as inosine, methyl-5-deoxycytidine, deoxyuridine, dimethylamino-5-deoxyuridine, or diamino-2, 6-purine. Sugar or phosphate residues may also be modified or substituted. For example, a deoxyribose residue may be replaced by a polyamide (Nielsen et al., Science (1991) 254:1497) and phosphate residues may be replaced by ester groups such as diphosphate, alkyl, arylphosphonate and phosphorothioate esters. In addition, the 2'-hydroxyl group on ribonucleotides may be modified by including such groups as alkyl groups.

Probes of the invention are used in diagnostic tests, as capture or detection probes. Such capture probes are conventionally immobilized on a solid support, directly or indirectly, by covalent means or by passive adsorption. A detection probe is labelled by a detection marker selected from: radioactive isotopes, enzymes such as peroxidase, alkaline phosphatase, and enzymes able to hydrolyze a chromogenic, fluorogenic, or luminescent substrate, compounds that are chromogenic, fluorogenic, or luminescent, nucleotide base analogs, and biotin.

Probes of the invention are used in any conventional hybridization technique, such as dot blot (Maniatis et al., Molecular Cloning: A Laboratory Manual (1982) Cold Spring Harbor Laboratory Press, Cold Spring Harbor, N.Y.), Southern blot (Southern, J. Mol. Biol. (1975) 98:503), northern blot (identical to Southern blot with the exception that RNA is used as a target), or the sandwich technique (Dunn et al., Cell (1977) 12:23). The latter technique involves the use of a specific capture probe and/or a specific detection probe with nucleotide sequences that at least partially differ from each other.

A primer is a probe of usually about 10 to about 40 nucleotides that is used to initiate enzymatic polymerization of DNA in an amplification process (e.g., PCR), in an elongation process, or in a reverse transcription method. Primers used in diagnostic methods involving PCR are labeled by methods known in the art.

As described herein, the invention also encompasses (i) a reagent comprising a probe of the invention for detecting and/or identifying the presence of *Chlamydia* in a biological material; (ii) a method for detecting and/or identifying the presence of *Chlamydia* in a biological material, in which (a) a sample is recovered or derived from the biological material, (b) DNA or RNA is extracted from the material and denatured, and (c) exposed to a probe of the invention, for example, a capture, detection probe or both, under stringent hybridization conditions, such that hybridization is detected; and (iii) a method for detecting and/or identifying the presence of *Chlamydia* in a biological material, in which (a) a sample is recovered or derived from the biological material, (b) DNA is extracted therefrom, (c) the extracted DNA is primed with at least one, and preferably two, primers of the invention and amplified by polymerase chain reaction, and (d) the amplified DNA fragment is produced.

It is apparent that disclosure of polynuclectide sequences of SEQ ID No: 1, its homologs and partial sequences enable their corresponding amino acid sequences. Accordingly, a sixth aspect of the invention features a substantially purified polypeptide or polypeptide derivative having an amino acid sequence encoded by a polynucleotide of the invention.

A "substantially purified polypeptide" as used herein is defined as a polypeptide that is separated from the environment in which it naturally occurs and/or that is free of the majority of the polypeptides that are present in the environment in which it was synthesized. For example, a substantially purified polypeptide is free from cytoplasmic polypeptides. Those skilled in the art would readily understand that the polypeptides of the invention may be purified from a natural source, i.e., a *Chlamydia* strain, or produced by recombinant means.

Consistent with the sixth aspect of the invention are polypeptides, homologs or fragments which are modified or treated to enhance their immunogenicity in the target animal, in whom the polypeptide, homolog or fragments are intended to confer protection against *Chlamydia*. Such modifications or treatments include: amino acid substitutions with an amino acid derivative such as 3-methyhistidine, 4-hydroxyproline, 5-hydroxylysine etc., modifications or deletions which are carried out after preparation of the polypeptide, homolog or fragment, such as the modification of free amino, carboxyl or hydroxyl side groups of the amino acids.

Identification of homologous polypeptides or polypeptide derivatives encoded by polynucleotides of the invention which have specific antigenicity is achieved by screening for cross-reactivity with an antiserum raised against the polypeptide of reference having an amino acid sequence of SEQ ID No: 1. The procedure is as follows: a monospecific hyperimmune antiserum is raised against a purified reference polypeptide, a fusion polypeptide (for example, an expression product of MBP, GST, or His-tag systems, the description and instructions for use of which are contained in Invitrogen product manuals for pcDNA3.1/Myc-His(+) A, B, and C and for the Xpress™ System Protein Purification), or a synthetic peptide predicted to be antigenic. Where an ant-serum is raised against a fusion polypeptide, two different fusion systems are employed. Specific antigenicity can be determined according to a number of methods, including Western blot (Towbin et al., Proc. Natl. Acad. Sci. USA (1979) 76:4350), dot blot, and ELISA, as described below.

In a Western blot assay, the product to be screened, either as a purified preparation or a total *E. coli* extract, is submitted to SDS-Page electrophoresis as described by Laemmli (Nature (1970) 227:680). After transfer to a nitrocellulose membrane, the material is further incubated with the monospecific hyperimmune antiserum diluted in the range of dilutions from about 1:5 to about 1:5000, preferably from about 1:100 to about 1:500. Specific antigenicity is shown once a band corresponding to the product exhibits reactivity at any of the dilutions in the above range.

In an ELISA assay, the product to be screened is preferably used as the coating antigen. A purified preparation is preferred, although a whole cell extract can also be used. Briefly, about 100 µl of a preparation at about 10 µg protein/ml are distributed into wells of a 96-well polycarbonate ELISA plate. The plate is incubated for 2 hours at 37° C. then overnight at 4° C. The plate is washed with phosphate buffer saline (PBS) containing 0.05% Tween 20 (PBS/Tween buffer). The wells are saturated with 250 µl PBS containing 1% bovine serum albumin (BSA) to prevent non-specific antibody binding. After 1 hour incubation at 37° C., the plate is washed with PBS/Tween buffer. The antiserum is serially diluted in PBS/Tween buffer containing 0.5% BSA. 100 µl of dilutions are added per well. The plate is incubated for 90 minutes at 37° C., washed and evaluated according to standard procedures. For example, a goat anti-rabbit peroxidase conjugate is added to the wells when specific antibodies were raised in rabbits. Incubation is carried out for 90 minutes at 37° C. and the plate is washed. The reaction is developed with the appropriate substrate and the reaction is measured by colorimetry (absorbance measured spectrophotometrically). Under the above experimental conditions, a positive reaction is shown by O.D. values greater than a non immune control serum.

In a dot blot assay, a purified product is preferred, although a whole cell extract can also be used. Briefly, a solution of the product at about 100 µg/ml is serially two-fold diluted in 50 mM Tris-HCl (pH 7.5). 100 µl of each dilution are applied to a nitrocellulose membrane 0.45 µm set in a 96-well dot blot apparatus (Biorad). The buffer is removed by applying vacuum to the system. Wells are washed by addition of 50 mM Tris-HCl (pH 7.5) and the membrane is air-dried. The membrane is saturated in blocking buffer (50 mM Tris-HCl (pH 7.5) 0.15 M NaCl, 10 g/L skim milk) and incubated with an antiserum dilution from about 1:50 to about 1:5000, preferably about 1:500. The reaction is revealed according to standard procedures. For example, a goat anti-rabbit peroxidase conjugate is added to the wells when rabbit antibodies are used. Incubation is carried out 90 minutes at 37° C. and the blot is washed. The reaction is developed with the appropriate substrate and stopped. The reaction is measured visually by the appearance of a colored spot, e.g., by colorimetry. Under the above experimental conditions, a positive reaction is shown once a colored spot is associated with a dilution of at least about 1:5, preferably of at least about 1:500.

Therapeutic or prophylactic efficacy of a polypeptide or derivative of the invention can be evaluated as described below. A seventh aspect of the invention provides (i) a composition of matter comprising a polypeptide of the invention together with a diluent or carrier; specifically (ii) a pharmaceutical composition containing a therapeutically or prophylactically effective amount of a polypeptide of the invention; (iii) a method for inducing an immune response against *Chlamydia* in a mammal, by administering to the mammal an immunogenically effective amount of a polypeptide of the invention to elicit a protective immune response to *Chlamydia*; and particularly, (iv). a method for preventing and/or treating a *Chlamydia* (e.g., *C. trachomatis. C. psittaci, C. pneumoniae*. or *C. pecorum*) infection, by administering a prophylactic or therapeutic amount of a polypeptide of the invention to an infected individual. Additionally, the seventh aspect of the invention encompasses the use of a polypeptide of the invention in the preparation of a medicament for preventing and/or treating *Chlamydia* infection.

As used herein, the immunogenic compositions of the invention are administered by conventional routes known the vaccine field, in particular to a mucosal (e.g., ocular, intranasal, pulmonary, oral, gastric, intestinal, rectal, vaginal, or urinary tract) surface or via the parenteral (e.g., subcutaneous, intradermal, intramuscular, intravenous, or intraperitoneal) route. The choice of administration route depends upon a number of parameters, such as the adjuvant associated with the polypeptide. If a mucosal adjuvant is used, the intranasal or oral route is preferred. If a lipid formulation or an aluminum compound is used, the parenteral route is preferred with the sub-cutaneous or intramuscular route being most preferred. The choice also depends upon the nature of the vaccine agent. For example, a polypeptide of the invention fused to CTB or LTB is best administered to a mucosal surface.

As used herein, the composition of the invention contains one or several polypeptides or derivatives of the invention. The composition optionally contains at least one additional *Chlamydia* antigen, or a subunit, fragment, homolog, mutant, or derivative thereof.

For use in a composition of the invention, a polypeptide or derivative thereof is formulated into or with liposomes, preferably neutral or anionic liposomes, microspheres, ISCOMS, or virus-like-particles (VLPs) to facilitate delivery and/or enhance the immune response. These compounds are readily available to one skilled in the art; for example, see Liposomes: A Practical Approach, RCP New Ed, IRL press (1990).

Adjuvants other than liposomes and the like are also used and are known in the art. Adjuvants may protect the antigen from rapid dispersal by sequestering it in a local deposit, or they may contain substances that stimulate the host to secrete factors that are chemotactic for macrophages and other components of the immune system. An appropriate selection can conventionally be made by those skilled in the art, for example, from those described below (under the eleventh aspect of the invention).

Treatment is achieved in a single dose or repeated as necessary at intervals, as can be determined readily by one skilled in the art. For example, a priming dose is followed by three booster doses at weekly or monthly intervals. An appropriate dose depends on various parameters including the recipient (e.g., adult or infant), the particular vaccine antigen, the route and frequency of administration, the presence/absence or type of adjuvant, and the desired effect (e.g., protection and/or treatment), as can be determined by one skilled in the art. In general, a vaccine antigen of the invention is administered by a mucosal route in an amount from about 10 µg to about 500 mg, preferably from about 1 mg to about 200 mg. For the parenteral route of administration, the dose usually does not exceed about 1 mg, preferably about 100 µg.

When used as vaccine agents, polynucleotides and polypeptides of the invention may be used sequentially as part of a multistep immunization process. For example, a mammal is initially primed with a vaccine vector of the invention such as a pox virus, e.g., via the parenteral route, and then boosted twice with the polypeptide encoded by the vaccine vector, e.g., via the mucosal route. In another example, liposomes associated with a polypeptide or derivative of the invention is also used for priming, with boosting being carried out mucosally using a soluble polypeptide or derivative of the invention in combination with a mucosal adjuvant (e.g., LT).

A polypeptide derivative of the invention is also used in accordance with the seventh aspect as a diagnostic reagent for detecting the presence of anti-*Chlamydia* antibodies, e.g., in a blood sample. Such polypeptides are about 5 to about 80, preferably about 10 to about 50 amino acids in length. They are either labeled or unlabeled, depending upon the diagnostic method. Diagnostic methods involving such a reagent are described below.

Upon expression of a DNA molecule of the invention, a polypeptide or polypeptide derivative is produced and purified using known laboratory techniques. As described above, the polypeptide or polypeptide derivative may be produced as a fusion protein containing a fused tail that facilitates purification. The fusion product is used to immunize a small mammal, e.g., a mouse or a rabbit, in order to raise antibodies against the polypeptide or polypeptide derivative (monospecific antibodies). Accordingly, an eighth aspect of the invention provides a monospecific antibody that binds to a polypeptide or polypeptide derivative of the invention.

By "monospecific antibody" is meant an antibody that is capable of reacting with a unique naturally-occurring *Chlamydia* polypeptide. An antibody of the invention is either polyclonal or monoclonal. Monospecific antibodies may be recombinant, e.g., chimeric (e.g., constituted by a variable region of murine origin associated with a human constant region), humanized (a human immunoglobulin constant backbone together with hypervariable region of animal, e.g., murine, origin), and/or single chain. Both polyclonal and monospecific antibodies may also be in the form of immunoglobulin fragments, e.g., F(ab)'2 or Fab fragments. The antibodies of the invention are of any isotype, e.g., IgG or IgA, and polyclonal antibodies are of a single isotype or a mixture of isotypes.

Antibodies against the polypeptides, homologs or fragments of the present invention are generated by immunization of a mammal with a composition comprising said polypeptide, homolog or fragment. Such antibodies may be polyclonal or monoclonal. Methods to produce polyclonal or monoclonal antibodies are well known in the art. For a review, see "Antibodies, A Laboratory Manual, Cold Spring Harbor Laboratory, Eds. E. Harlow and D. Lane (1988), and D. E. Yelton et al., 1981. Ann. Rev. Biochem. 50:657–680. For monoclonal antibodies, see Kohler & Milstein (1975) Nature 256:495–497.

The antibodies of the invention, which are raised to a polypeptide or polypeptide derivative of the invention, are produced and identified using standard immunological assays, e.g., Western blot analysis, dot blot assay, or ELISA (see, e.g., Coligan et al., Current Protocols in Immunology (1994) John Wiley & Sons, Inc., New York, N.Y.). The antibodies are used in diagnostic methods to detect the presence of a *Chlamydia* antigen in a sample, such as a biological sample. The antibodies are also used in affinity chromatography for purifying a polypeptide or polypeptide derivative of the invention. As is discussed further below, such antibodies may be used in prophylactic and therapeutic passive immunization methods.

Accordingly, a ninth aspect of the invention provides (i) a reagent for detecting the presence of *Chlamydia* in a biological sample that contains an antibody, polypeptide, or polypeptide derivative of the invention; and (ii) a diagnostic method for detecting the presence of *Chlamydia* in a biological sample, by contacting the biological sample with an antibody, a polypeptide, or a polypeptide derivative of the invention, such that an immune complex is formed, and by detecting such complex to indicate the presence of *Chlamydia* in the sample or the organism from which the sample is derived.

Those skilled in the art will readily understand that the immune complex is formed between a component of the sample and the antibody, polypeptide, or polypeptide derivative, whichever is used, and that any unbound material is removed prior to detecting the complex. It is understood that a polypeptide reagent is useful for detecting the presence of anti-*Chlamydia* antibodies in a sample, e.g., a blood sample, while an antibody of the invention is used for screening a sample, such as a gastric extract or biopsy, for the presence of *Chlamydia* polypeptides.

For diagnostic applications, the reagent (i.e., the antibody, polypeptide, or polypeptide derivative of the invention) is either in a free state or immobilized on a solid support, such as a tube, a bead, or any other conventional support used in the field. Immobilization is achieved using direct or indirect means. Direct means include passive adsorption (ton-covalent binding) or covalent binding between the support and the reagent. By "indirect means" is meant that an anti-reagent compound that interacts with a reagent is first attached to the solid support. For example, if a polypeptide reagent is used, an antibody that binds to it can serve as an anti-reagent, provided that it binds to an epitope that is not involved in the recognition of antibodies in biological samples. Indirect means may also employ a ligand-receptor system, for example, where a molecule such as a vitamin is grafted onto the polypeptide reagent and the corresponding receptor immobilized on the solid phase. This is illustrated by the biotin-streptavidin system. Alternatively, a peptide tail is added chemically or by genetic engineering to the reagent and the grafted or fused product immobilized by passive adsorption or covalent linkage of the peptide tail.

Such diagnostic agents may be included in a kit which also comprises instructions for use. The reagent is labeled with a detection means which allows for the detection of the reagent when it is bound to its target. The detection means may be a fluorescent agent such as fluorescein isocyanate or fluorescein isothiocyanate, or an enzyme such as horse radish peroxidase or luciferase or alkaline phosphatase, or a radioactive element such as $^{125}$I or $^{51}$Cr.

Accordingly, a tenth aspect of the invention provides a process for purifying, from a biological sample, a polypeptide or polypeptide derivative of the invention, which involves carrying out antibody-based affinity chromatography with the biological sample, wherein the antibody is a monospecific antibody of the invention.

For use in a purification process of the invention, the antibody,is either polyclonal or monospecific, and preferably is of the IgG type. Purified IgGs is prepared from an antiserum using standard methods (see, e.g., Coligan et al., Current Protocols in Immunology (1994) John Wiley & Sons, Inc., New York, N.Y.). Conventional chromatography supports, as well as standard methods for grafting antibodies, are described in, e.g., Antibodies: A Laboratory Manual, D. Lane, E. Harlow, Eds. (1988) and outlined below.

Briefly, a biological sample, such as an *C. pneumoniae* extract preferably in a buffer solution, is applied to a chromatography material, preferably equilibrated with the buffer used to dilute the biological sample so that the polypeptide or polypeptide derivative of the invention (i.e., the antigen) is allowed to adsorb onto the material. The chromatography material, such as a gel or a resin coupled to an antibody of the invention, is in either a batch form or a column. The unbound components are washed off and the antigen is then eluted with an appropriate elution buffer, such as a glycine buffer or a buffer containing a chaotropic agent, e.g:, guanidine HCl, or high salt concentration (e.g., 3 M MgCl$_2$). Eluted fractions are recovered and the presence of the antigen is detected, e.g., by measuring the absorbance at 280 nm.

An eleventh aspect of the invention provides (i) a composition of matter comprising a monospecific antibody of the invention, together with a diluent or carrier; (ii) a pharmaceutical composition comprising a therapeutically or prophylactically effective amount of a monospecific antibody of the invention, and (iii) a method for treating or preventing a *Chlamydia* (e.g., *C. trachomatis, C. psittaci, C. pneumoniae* or *C. pecorum*) infection, by administering a therapeutic or prophylactic amount of a monospecific antibody of the invention to an infected individual. Additionally, the eleventh aspect of the invention encompasses the use of a monospecific antibody of the invention in the preparation of a medicament for treating or preventing *Chlamydia* infection.

The monospecific antibody is either polyclonal or monoclonal, preferably of the IgA isotype (predominantly). In passive immunization, the antibody is administered to a mucosal surface of a mammal, e.g., the gastric mucosa, e.g., orally or intragastrically, advantageously, in the presence of a bicarbonate buffer. Alternatively, systemic administration, not requiring a bicarbonate buffer, is carried out. A monospecific antibody of the invention is administered as a single active component or as a mixture with at least one monospecific antibody specific for a different *Chlamydia* polypeptide. The amount of antibody and the particular regimen used are readily determined by one skilled in the art. For example, daily administration of about 100 to 1,000 mg of antibodies over one week, or three doses per day of about 100 to 1,000 mg of antibodies over two or three days, are effective regimens for most purposes.

Therapeutic or prophylactic efficacy are evaluated using standard methods in the art, e.g., by measuring induction of a mucosal immune response or induction of protective and/or therapeutic immunity, using, e.g., the *C. pneumoniae* mouse model. Those skilled in the art will readily recognize that the *C. pneumoniae* strain of the model may be replaced with another *Chlamydia* strain. For example, the efficacy of DNA molecules and polypeptides from *C. pneumoniae* is preferably evaluated in a mouse model using *C. pneumoniae* strain. Protection is determined by comparing the degree of *Chlamydia* infection to that of a control group. Protection is shown when infection is reduced by comparison to the control group. Such an evaluation is made for polynucleotides, vaccine vectors, polypeptides and derivatives thereof, as well as antibodies of the invention.

Adjuvants useful in any of the vaccine compositions described above are as follows.

Adjuvants for parenteral administration include aluminum compounds, such as aluminum hydroxide, aluminum phosphate, and aluminum hydroxy phosphate. The antigen is precipitated with, or adsorbed onto, the aluminum compound according to standard protocols. Other adjuvants, such as RIBI (ImmunoChem, Hamilton, Mont.), are used in parenteral administration.

Adjuvants for mucosal administration include bacterial toxins, e.g., the cholera toxin (CT), the *E. coli* heat-labile toxin (LT), the *Clostridium difficile* toxin A and the pertussis toxin (PT), or combinations, subunits, toxoids, or mutants thereof such as a purified preparation of native cholera toxin subunit B (CTB). Fragments, homologs, derivatives, and fusions to any of these toxins are also suitable, provided that they retain adjuvant activity. Preferably, a mutant having reduced toxicity is used. Suitable mutants are described, e.g., in WO 95/17211 (Arg-7-Lys CT mutant), WO 96/06627 (Arg-192-Gly LT mutant), and WO 95/34323 (Arg-9-Lys and Glu-129-Gly PT mutant). Additional LT mutants that are used in the methods and compositions of the invention include, e.g., Ser-63-Lys, Ala-69Gly, Glu-110-Asp, and Glu-112-Asp mutants. Other adjuvants, such as a bacterial monophosphoryl lipid A (MPLA) of, e.g., *E. coli, Salmonella minnesota, Salmonella typhimurium,* or *Shigella flexneri;* saponins, or polylactide glycolide (PLGA) microspheres, is also be used in mucosal administration.

Adjuvants useful for both mucosal and parenteral administrations include polyphosphazene (WO 95/02415), DC-chol (3 b-(N-(N',N'-dimethyl aminomethane)-carbamoyl) cholesterol; U.S. Pat. No. 5,283,185 and WO 96/14831) and QS-21 (WO 88/09336).

Any pharmaceutical composition of the invention containing a polynucleotide, a polypeptide, a polypeptide derivative, or an antibody of the invention, is manufactured in a conventional manner. In particular, it is formulated with a pharmaceutically acceptable diluent or carrier, e.g., water or a saline solution such as phosphate buffer saline. In general, a diluent or carrier is selected on the basis of the mode and route of administration, and standard pharmaceutical practice. Suitable pharmaceutical carriers or diluents, as well as pharmaceutical necessities for their use in pharmaceutical formulations, are described in *Remington's Pharmaceutical Sciences,* a standard reference text in this field and in the USP/NF.

The invention also includes methods in which *Chlamydia* infection are treated by oral administration of a *Chlamydia* polypeptide of the invention and a mucosal adjuvant, in combination with an antibiotic, an antacid, sucralfate, or a combination thereof. Examples of such compounds that can be administered with the vaccine antigen and the adjuvant are antibiotics, including, e.g., macrolides, tetracyclines, and derivatives thereof (specific examples of antibiotics that can be used include azithromycin or doxicyclin or immunomodulators such as cytokines or steroids). In addition, compounds containing more than one of the above-listed components coupled together, are used. The invention also includes compositions for carrying out these methods, i.e., compositions containing a *Chlamydia* antigen (or antigens) of the invention, an adjuvant, and one or more of the above-listed compounds, in a pharmaceutically acceptable carrier or diluent.

It has recently been shown that the 60 kDa cysteine rich membrane protein contains a sequence cross-reactive with the murine alpha-myosin heavy chain epitope M7A-alpha, an epitope conserved in humans (Bachmaier et al., Science (1999) 283:1335). This cross-reactivity is proposed to contribute to the development of cardiovascular disease, so it may be beneficial to remove this epitope, and any other epitopes cross-reactive with human antigens, from the protein if it is to be used as a vaccine. Accordingly, a further embodiment of the present invention includes the modification of the coding sequence, for example, by deletion or substitution of the nucleotides encoding the epitope from polynucleotides encoding the protein, as to improve the efficacy and safety of the protein as a vaccine. A similar approach may be appropriate for any protective antigen found to have unwanted homologies or cross-reactivities with human antigens.

Amounts of the above-listed compounds used in the methods and compositions of the invention are readily determined by one skilled in the art. Treatment/immunization schedules are also known and readily designed by one skilled in the art. For example, the non-vaccine components can be administered on days 1–14, and the vaccine antigen+ adjuvant can be administered on days 7, 14, 21, and 28.

EXAMPLES

The above disclosure generally describes the present invention. A more complete understanding can be obtained by reference to the following specific examples. These examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

Example 1

This example illustrates the preparation of plasmid vector pCACPNM209 containing the ATP-binding cassette gene.

The ATP-binding cassette gene was amplified from *Chlamydia pneumoniae* genomic DNA strain CWLO29 by polymerase chain reaction (PCR) using a 5' primer (5' ATAAGAAT GCGGCCGCCACCATGCGCAAGATATCAGTGGGAATC 3'; SEQ ID No: 3) and a 3' primer (5' GCGCC GGATCCCATTTTCCTTAGCATAACGGAAGTCC 3'; SEQ ID No: 4). The 5' primer contains a NotI restriction site, a ribosome binding site, an initiation codon and a sequence at the 5' end of the ATP-binding cassette coding sequence. The 3' primer includes the sequence encoding the C-terminal sequence of the ATP-binding cassette gene and a BamHI restriction site. The stop codon was excluded and an additional nucleotide was inserted to obtain an in-frame fusion with the Histidine tag.

After amplification, the PCR fragment was purified using QIAquick™ PCR purification kit (Qiagen), digested with NotI and BamHI and cloned into the pCA-Myc-His eukaryotic expression vector described in Example 2 (FIG. 3) with transcription under control of the human CMV promoter.

Example 2

This example illustrates the preparation of the eukaryotic expression vector pCA/Myc-His.

Plasmid pcDNA3.1(−)Myc-His C (Invitrogen) was restricted with SpeI and BamHI to remove the CMV promoter and the remaining vector fragment was isolated. The CMV promoter and intron A from plasmid VR-1012 (Vical) was isolated on a SpeI/BamHI fragment. The fragments were ligated together to produce plasmid pCA/Myc-His. The NotI/BamHI restricted PCR fragment containing the ATP-binding cassette gene was ligated into the NotI and BamHI restricted plasmid pCA/Myc-His to produce plasmid pCACPNM209 (FIG. 3).

The resulting plasmid, pCACPNM209, was transferred by electroporation into *E. coli* XL-1 blue (Stratagene) which was grown in LB broth containing 50 μg/ml carbenicillin. The plasmid was isolated by the Endo Free Plasmid Giga Kit™ (Qiagen) large scale DNA purification system. DNA concentration was determined by absorbance at 260 nm and the plasmid was verified after gel electrophoresis and ethidium bromide staining by comparison to molecular weight standards. The 5' and 3' ends of the gene were verified by sequencing using a LiCor model 4000 L DNA sequencer and IRD-800 labelled primers.

Example 3

This example illustrates the immunization of mice to achieve protection against an intranasal challenge of *C. pneumoniae.*

It has been previously demonstrated (Yang et al. Infect. Immun. May 1993. 61(5):2037–40) that mice are susceptible to intranasal infection with different isolates of *C. pneumoniae.* Strain AR-39 (Grayston et al (1990) Journal of Infectious Diseases 161:618–625) was used in Balb/c mice as a challenge infection model to examine the capacity of *Chlamydia* gene products delivered as naked DNA to elicit a protective response against a sublethal *C. pneumoniae* lung infection. Protective immunity is defined as an accelerated clearance of pulmonary infection.

Groups of 7 to 9 week old male Balb/c mice (8 to 10 per group) were immunized intramuscularly (i.m.) plus intranasally (i.n.) with plasmid DNA containing the *C. pneumoniae* ATP-binding cassette gene as described in Examples 1 and 2. Saline or the plasmid vector lacking an inserted *Chlamydial* gene was given to groups of control animals.

For i.m. immunization, alternate left and right quadriceps were injected with 100 μg of DNA in 50 μl of PBS on three occasions at 0, 3 and 6 weeks. For i.n. immunization, anaesthetized mice were aspirated 50 μl of PBS containing 50 μg DNA on three occasions at 0, 3 and 6 weeks. At week 8, immunized mice were inoculated i.n. with $5\times10^5$ IFU of *C. pneumoniae,* strain AR39 in 100 μl of SPG buffer to test their ability to limit the growth of a sublethal *C. pneumoniae* challenge.

Lungs were taken from mice at day 9 post-challenge and immediately homogenised in SPG buffer (7.5% sucrose, 5 mM glutamate, 12.5 mM phosphate pH7.5). The homogenate was stored frozen at −70° C. until assay. Dilutions of the homogenate were assayed for the presence of infectious *Chlamydia* by inoculation onto monolayers of susceptible cells. The inoculum was centrifuged onto the cells at 3000 rpm for 1 hour, then the cells were incubated for three days at 35° C. in the presence of 1 μg/ml cycloheximide. After incubation the monolayers were fixed with formalin and methanol then immunoperoxidase stained for the presence of *Chlamydial* inclusions using convalescent sera from rabbits infected with *C. pneumoniae* and metal-enhanced DAB as a peroxidase substrate.

FIG. 4 and Table 1 show that mice immunized i.n. and i.m. with pCACPNM209 had *Chlamydial* lung titers less than 61,000 in 4 of 6 cases at day 9 (mean 65,266), whereas the range of values for control mice sham immunized with saline was 61,100–300,500 IFU/lung (mean 164,537) at day 9. DNA immunisation per se was not responsible for the observed protective effect since another plasmid DNA construct, pCACPNM332, failed to protect, with lung titers in immunised mice similar to those obtained for saline-immunized control mice (mean 171,016). The construct pCACPNM332 is identical to pCACPNM209 except that the nucleotide sequence encoding the putative ATP-binding cassette is replaced with a *C. pneumoniae* nucleotide sequence encoding an unrelated hypothetical protein.

Example 4

This example illustrates the identification of B- and T-cell epitopes in the pCACPNM209 translated protein.

B-cell epitopes were identified based on the product of flexibilty and hydrophobicity propensities using the program SEQSEE (Wishart D S, et al. "SEQSEE: a comprehensive program suite for protein sequence analysis." *Comput Appl Biosci.* 1994 Apr;10(2):121–32) to identify external surface features (epitopes). These epitopes are shown in Table 2. T-cell epitopes for-HLA-A0201 MHC subclass were identified based on the algorithm of Parker et al. 1995 (Parker K C, et al. "Peptide binding to MHC-class I molecules: implications for antigenic peptide prediction." *Immunol Res* 1995;14(1):34–57).

TABLE 1

BACTERIAL LOAD (INCLUSION FORMING UNITS PER LUNG) IN THE LUNGS OF BALB/C MICE IMMUNIZED WITH VARIOUS DNA IMMUNIZATION CONSTRUCTS

| MOUSE | Saline Day 9 | pCACPNM332 Day 9 | pCACPNM209 Day 9 |
|---|---|---|---|
| 1 | 158700 | 166600 | 60300 |
| 2 | 239600 | 116100 | 97300 |
| 3 | 169800 | 350100 | 93700 |
| 4 | 163500 | 41300 | 56600 |
| 5 | 110700 | 145100 | 51500 |
| 6 | 107400 | 81500 | 32200 |
| 7 | 300500 | | |
| 8 | 66100 | | |
| MEAN | 64537.5 | 150116.667 | 65266.6667 |
| SD | 75627.0 | 107700.18 | 25366.49 |
| Wilcoxon p | | 0.662 | 0.0027 |

TABLE 2

Identified B- and T-cell epitopes from CPNM209

| B cell epitope | T cell epitope |
|---|---|
| 338 NIHSYPEHQKQEMAQRQAYAKK (SEQ ID No:5) | RLLSEISLV (SEQ ID No:7) |
| QNIEQEQDHQKRSE (SEQ ID No:6) | |

---

The invention claimed is:

1. A vaccine vector comprising an isolated nucleic acid molecule which encodes SEQ ID No: 2, wherein the nucleic acid molecule is operably linked to a promoter functional in a mammalian cell.

2. The vaccine vector of claim 1 further comprising another nucleic, acid encoding an additional polypeptide which enhances the immune response to the polypeptide having SEQ ID No: 2, wherein the additional polypeptide is a *Chlamydia* polypeptide.

3. The vaccine vector of claim 1 wherein the promoter is a viral promoter.

4. The vaccine vector of claim 2 wherein the promoter is a viral promoter.

5. The vaccine vector of claim 3 wherein the promoter is cytomegalovirus (CMV) promoter.

6. The vaccine vector of claim 4 wherein the promoter is cytomegalovirus (CMV) promoter.

7. The vaccine vector of claim 1 wherein the nucleotide sequence of the nucleic acid molecule which encodes SEQ ID No:2 is SEQ ID No:1.

8. The vaccine vector of claim 2 wherein the nucleotide sequence of the nucleic acid molecule which encodes SEQ ID No:2 is SEQ ID No:1.

9. The vaccine vector of claim 3 wherein the nucleotide sequence of the nucleic acid molecule which encodes SEQ ID No:2 is SEQ ID No:1.

10. The vaccine vector of claim 2 wherein the nucleotide sequence of the nucleic acid molecule which encodes SEQ ID No:2 is SEQ ID No:1.

11. The vaccine vector of claim 5 wherein the nucleotide sequence of the nucleic acid molecule which encodes SEQ ID No:2 is SEQ ID No:1.

12. The vaccine vector of claim 6 wherein the nucleotide sequence of the nucleic acid molecule which encodes SEQ ID No:2 is SEQ ID No:1.

13. A vaccine comprising the vaccine vector according to claim 1 and a pharmaceutically acceptable carrier.

14. A vaccine comprising the vaccine vector according to claim 2 and a pharmaceutically acceptable carrier.

15. A vaccine comprising the vaccine vector according to claim 3 and a pharmaceutically acceptable carrier.

16. A vaccine comprising the vaccine vector according to claim 4 and a pharmaceutically acceptable carrier.

17. A vaccine comprising the vaccine vector according to claim 5 and a pharmaceutically acceptable carrier.

18. A vaccine comprising the vaccine vector according to claim 6 and a pharmaceutically acceptable carrier.

19. A vaccine comprising the vaccine vector according to claim 7 and a pharmaceutically acceptable carrier.

20. A vaccine comprising the vaccine vector according to claim 8 and a pharmaceutically acceptable carrier.

21. A vaccine comprising the vaccine vector according to claim 1 and an adjuvant.

22. A vaccine comprising the vaccine vector according to claim 2 and an adjuvant.

23. A vaccine comprising the vaccine vector according to claim 3 and an adjuvant.

24. A vaccine comprising the vaccine vector according to claim 5 and an adjuvant.

25. The vaccine vector according to claim 1 in unit dosage form.

26. The vaccine vector according to claim 2 in unit dosage form.

27. The vaccine vector according to claim 3 in unit dosage form.

28. The vaccine vector according to claim 5 in unit dosage form.

29. The vaccine vector according to claim 1 which is unable to replicate in mammalian cells and unable to integrate substantially in a mammalian genome.

30. The vaccine vector according to claim 2 which is unable to replicate in mammalian cells and unable to integrate substantially in a mammalian genome.

31. The vaccine vector according to claim 3 which is unable to replicate in mammalian cells and unable to integrate substantially in a mammalian genome.

32. The vaccine vector according to claim 5 which is unable to replicate in mammalian cells and unable to integrate substantially in a mammalian genome.

33. The vaccine vector of claim 1 which is expression plasmid pCACPNM209 as shown in FIG. 3.

* * * * *

UNITED STATES PATENT AND TRADEMARK OFFICE
CERTIFICATE OF CORRECTION

| | |
|---|---|
| PATENT NO. | : 7,081,245 B2 |
| APPLICATION NO. | : 10/337423 |
| DATED | : July 25, 2006 |
| INVENTOR(S) | : Andrew D. Murdin et al. |

It is certified that error appears in the above-identified patent and that said Letters Patent is hereby corrected as shown below:

Column 39, line 28, claim 10, "...of claim 2..." should read --...of claim 4...--.

Signed and Sealed this

Sixth Day of February, 2007

JON W. DUDAS
*Director of the United States Patent and Trademark Office*

SEQUENCE LISTING

<160> NUMBER OF SEQ ID NOS: 7

<210> SEQ ID NO 1
<211> LENGTH: 1799
<212> TYPE: DNA
<213> ORGANISM: Chlamydia pneumoniae
<220> FEATURE:
<221> NAME/KEY: CDS
<222> LOCATION: (101)..(1696)

<400> SEQUENCE: 1

```
acttcccccc tgctaaacta tgctcagata atgctgctat gattgcaggt ctaggggag       60 aaaattttca aaaaactct agtattccgg aaattcgtat atg cgc aag ata tca      115
                                            Met Arg Lys Ile Ser
                                            1               5 gtg gga atc tgt atc acc att ctc ctt agc ctc tcc gta gtc ctc caa      163
Val Gly Ile Cys Ile Thr Ile Leu Leu Ser Leu Ser Val Val Leu Gln
            10              15                  20 ggc tgc aag gag tcc agt cac tcc tct aca tct cgg gga gaa ctc gct      211
Gly Cys Lys Glu Ser Ser His Ser Ser Thr Ser Arg Gly Glu Leu Ala
        25                  30                  35 att aat ata aga gat gaa ccc cgt tct tta gat cca aga caa gtg cga      259
Ile Asn Ile Arg Asp Glu Pro Arg Ser Leu Asp Pro Arg Gln Val Arg
```

|  |  |
|---|---|
| ctt ctt tca gaa atc agc ctt gtc aaa cat atc tat gag gga tta gtt<br>Leu Leu Ser Glu Ile Ser Leu Val Lys His Ile Tyr Glu Gly Leu Val<br>55              60                      65 | 307 |
| caa gaa aat aat ctt tca gga aat ata gag cct gct ctt gca gaa gac<br>Gln Glu Asn Asn Leu Ser Gly Asn Ile Glu Pro Ala Leu Ala Glu Asp<br>70                  75                    80                    85 | 355 |
| tac tct ctt tcc tcg gac gga ctc act tat act ttt aaa ctg aaa tca<br>Tyr Ser Leu Ser Ser Asp Gly Leu Thr Tyr Thr Phe Lys Leu Lys Ser<br>                    90                      95                    100 | 403 |
| gct ttt tgg agt aat ggc gac ccc tta aca gct gaa gac ttt ata gaa<br>Ala Phe Trp Ser Asn Gly Asp Pro Leu Thr Ala Glu Asp Phe Ile Glu<br>                  105                  110                  115 | 451 |
| tct tgg aaa caa gta gct act caa gaa gtc tca gga atc tat gct ttt<br>Ser Trp Lys Gln Val Ala Thr Gln Glu Val Ser Gly Ile Tyr Ala Phe<br>        120                  125                  130 | 499 |
| gcc ttg aat cca att aaa aat gta cga aag atc caa gag gga cac ctc<br>Ala Leu Asn Pro Ile Lys Asn Val Arg Lys Ile Gln Glu Gly His Leu<br>        135                  140                  145 | 547 |
| tcc ata gac cat ttt gga gtg cac tct cct aat gaa tct aca ctt gtt<br>Ser Ile Asp His Phe Gly Val His Ser Pro Asn Glu Ser Thr Leu Val<br>150                  155                  160                  165 | 595 |
| gtt acc ctg gaa tcc cca acc tcg cat ttc tta aaa ctt tta gct ctt<br>Val Thr Leu Glu Ser Pro Thr Ser His Phe Leu Lys Leu Leu Ala Leu<br>                  170                  175                  180 | 643 |
| cca gtc ttt ttc ccc gtt cat aaa tct caa aga acc ctg caa tcc aaa<br>Pro Val Phe Phe Pro Val His Lys Ser Gln Arg Thr Leu Gln Ser Lys<br>        185                  190                  195 | 691 |
| tct cta cct ata gca agc gga gct ttc tat cct aaa aat atc aaa caa<br>Ser Leu Pro Ile Ala Ser Gly Ala Phe Tyr Pro Lys Asn Ile Lys Gln<br>        200                  205                  210 | 739 |
| aaa caa tgg ata aaa ctc tca aaa aac cct cac tac tat aat caa agt<br>Lys Gln Trp Ile Lys Leu Ser Lys Asn Pro His Tyr Tyr Asn Gln Ser<br>        215                  220                  225 | 787 |
| cag gtg gaa act aaa acg att acg att cac ttc att ccc gat gca aac<br>Gln Val Glu Thr Lys Thr Ile Thr Ile His Phe Ile Pro Asp Ala Asn<br>230                  235                  240                  245 | 835 |
| aca gca gca aaa cta ttt aat cag gga aaa ctc aat tgg caa gga cct<br>Thr Ala Ala Lys Leu Phe Asn Gln Gly Lys Leu Asn Trp Gln Gly Pro<br>        250                  255                  260 | 883 |
| cct tgg gga gaa cgc att cct caa gaa acc cta tcc aat tta cag tct<br>Pro Trp Gly Glu Arg Ile Pro Gln Glu Thr Leu Ser Asn Leu Gln Ser<br>        265                  270                  275 | 931 |
| aag ggg cac tta cac tct ttt gat gtc gca gga acc tca tgg ctc acc<br>Lys Gly His Leu His Ser Phe Asp Val Ala Gly Thr Ser Trp Leu Thr<br>        280                  285                  290 | 979 |
| ttc aat atc aat aaa ttc ccc ctc aac aat atg aag ctt aga gaa gcc<br>Phe Asn Ile Asn Lys Phe Pro Leu Asn Asn Met Lys Leu Arg Glu Ala<br>        295                  300                  305 | 1027 |
| tta gca tca gcc tta gat aag gaa gct ctt gtc tca act ata ttc tta<br>Leu Ala Ser Ala Leu Asp Lys Glu Ala Leu Val Ser Thr Ile Phe Leu<br>310                  315                  320                  325 | 1075 |
| ggc cgt gca aaa act gcc gat cat ctc cta cct aca aat att cat agc<br>Gly Arg Ala Lys Thr Ala Asp His Leu Leu Pro Thr Asn Ile His Ser<br>        330                  335                  340 | 1123 |
| tat ccc gaa cat caa aaa caa gag atg gca caa cgc caa gct tac gct<br>Tyr Pro Glu His Gln Lys Gln Glu Met Ala Gln Arg Gln Ala Tyr Ala<br>        345                  350                  355 | 1171 |
| aaa aaa ctc ttt aaa gaa gct tta gaa gaa ctc caa atc act gct aaa | 1219 |

-continued

```
Lys Lys Leu Phe Lys Glu Ala Leu Glu Glu Leu Gln Ile Thr Ala Lys
        360                 365                 370 gat ctc gaa cat ctt aat ctt atc ttt ccc gtt tcc tcg tca gca agt    1267
Asp Leu Glu His Leu Asn Leu Ile Phe Pro Val Ser Ser Ser Ala Ser
    375                 380                 385 tct tta cta gtc caa ctt ata cga gaa cag tgg aaa gaa agt tta ggg    1315
Ser Leu Leu Val Gln Leu Ile Arg Glu Gln Trp Lys Glu Ser Leu Gly
390                 395                 400                 405 ttc gct atc cct att gtc gga aag gaa ttt gct ctt ctc caa gca gac    1363
Phe Ala Ile Pro Ile Val Gly Lys Glu Phe Ala Leu Leu Gln Ala Asp
                410                 415                 420 cta tct tca ggg aac ttc tct tta gct aca gga gga tgg ttc gca gac    1411
Leu Ser Ser Gly Asn Phe Ser Leu Ala Thr Gly Gly Trp Phe Ala Asp
            425                 430                 435 ttt gct gat cct atg gca ttt cta acg atc ttt gct tat cca tca gga    1459
Phe Ala Asp Pro Met Ala Phe Leu Thr Ile Phe Ala Tyr Pro Ser Gly
        440                 445                 450 gtt cct cct tat gca atc aac cat aag gac ttc cta gaa att cta caa    1507
Val Pro Pro Tyr Ala Ile Asn His Lys Asp Phe Leu Glu Ile Leu Gln
    455                 460                 465 aac ata gaa caa gag caa gat cac caa aaa cgc tcg gaa tta gtg tcg    1555
Asn Ile Glu Gln Glu Gln Asp His Gln Lys Arg Ser Glu Leu Val Ser
470                 475                 480                 485 caa gct tct ctt tac cta gag acc ttt cat att att gag ccg atc tac    1603
Gln Ala Ser Leu Tyr Leu Glu Thr Phe His Ile Ile Glu Pro Ile Tyr
                490                 495                 500 cac gac gca ttt caa ttt gct atg aat aaa aaa ctt tct aat cta gga    1651
His Asp Ala Phe Gln Phe Ala Met Asn Lys Lys Leu Ser Asn Leu Gly
            505                 510                 515 gtc tca cca aca gga gtt gtg gac ttc cgt tat gct aag gaa aat        1696
Val Ser Pro Thr Gly Val Val Asp Phe Arg Tyr Ala Lys Glu Asn
        520                 525                 530 tagcacctct tttaatctcg caaacttgtc aagaactgaa tcttatacta aactgggtgc    1756
ctttgtggca cctcgtttcc ttctgactgc tcttctctct cta                      1799
```

<210> SEQ ID NO 2
<211> LENGTH: 532
<212> TYPE: PRT
<213> ORGANISM: Chlamydia pneumoniae
<220> FEATURE:
<221> NAME/KEY: SITE
<222> LOCATION: (53)...(61)
<223> OTHER INFORMATION: T-cell epitope
<220> FEATURE:
<221> NAME/KEY: SITE
<222> LOCATION: (338)...(359)
<223> OTHER INFORMATION: B-cell epitope
<220> FEATURE:
<221> NAME/KEY: SITE
<222> LOCATION: (469)...(482)
<223> OTHER INFORMATION: B-cell epitope

<400> SEQUENCE: 2

```
Met Arg Lys Ile Ser Val Gly Ile Cys Ile Thr Ile Leu Leu Ser Leu
1               5                   10                  15

Ser Val Val Leu Gln Gly Cys Lys Glu Ser Ser His Ser Ser Thr Ser
            20                  25                  30

Arg Gly Glu Leu Ala Ile Asn Ile Arg Asp Glu Pro Arg Ser Leu Asp
        35                  40                  45

Pro Arg Gln Val Arg Leu Leu Ser Glu Ile Ser Leu Val Lys His Ile
    50                  55                  60
```

-continued

```
Tyr Glu Gly Leu Val Gln Glu Asn Asn Leu Ser Gly Asn Ile Glu Pro
 65                  70                  75                  80

Ala Leu Ala Glu Asp Tyr Ser Leu Ser Ser Asp Gly Leu Thr Tyr Thr
                 85                  90                  95

Phe Lys Leu Lys Ser Ala Phe Trp Ser Asn Gly Asp Pro Leu Thr Ala
            100                 105                 110

Glu Asp Phe Ile Glu Ser Trp Lys Gln Val Ala Thr Gln Glu Val Ser
            115                 120                 125

Gly Ile Tyr Ala Phe Ala Leu Asn Pro Ile Lys Asn Val Arg Lys Ile
130                 135                 140

Gln Glu Gly His Leu Ser Ile Asp His Phe Gly Val His Ser Pro Asn
145                 150                 155                 160

Glu Ser Thr Leu Val Val Thr Leu Glu Ser Pro Thr Ser His Phe Leu
                165                 170                 175

Lys Leu Leu Ala Leu Pro Val Phe Phe Pro Val His Lys Ser Gln Arg
            180                 185                 190

Thr Leu Gln Ser Lys Ser Leu Pro Ile Ala Ser Gly Ala Phe Tyr Pro
            195                 200                 205

Lys Asn Ile Lys Gln Lys Gln Trp Ile Lys Leu Ser Lys Asn Pro His
210                 215                 220

Tyr Tyr Asn Gln Ser Gln Val Glu Thr Lys Thr Ile Thr Ile His Phe
225                 230                 235                 240

Ile Pro Asp Ala Asn Thr Ala Ala Lys Leu Phe Asn Gln Gly Lys Leu
                245                 250                 255

Asn Trp Gln Gly Pro Pro Trp Gly Glu Arg Ile Pro Gln Glu Thr Leu
            260                 265                 270

Ser Asn Leu Gln Ser Lys Gly His Leu His Ser Phe Asp Val Ala Gly
            275                 280                 285

Thr Ser Trp Leu Thr Phe Asn Ile Asn Lys Phe Pro Leu Asn Asn Met
290                 295                 300

Lys Leu Arg Glu Ala Leu Ala Ser Ala Leu Asp Lys Glu Ala Leu Val
305                 310                 315                 320

Ser Thr Ile Phe Leu Gly Arg Ala Lys Thr Ala Asp His Leu Leu Pro
                325                 330                 335

Thr Asn Ile His Ser Tyr Pro Glu His Gln Lys Gln Glu Met Ala Gln
            340                 345                 350

Arg Gln Ala Tyr Ala Lys Lys Leu Phe Lys Glu Ala Leu Glu Glu Leu
            355                 360                 365

Gln Ile Thr Ala Lys Asp Leu Glu His Leu Asn Leu Ile Phe Pro Val
370                 375                 380

Ser Ser Ser Ala Ser Ser Leu Leu Val Gln Leu Ile Arg Glu Gln Trp
385                 390                 395                 400

Lys Glu Ser Leu Gly Phe Ala Ile Pro Ile Val Gly Lys Glu Phe Ala
                405                 410                 415

Leu Leu Gln Ala Asp Leu Ser Ser Gly Asn Phe Ser Leu Ala Thr Gly
            420                 425                 430

Gly Trp Phe Ala Asp Phe Asp Pro Met Ala Phe Leu Thr Ile Phe
            435                 440                 445

Ala Tyr Pro Ser Gly Val Pro Pro Tyr Ala Ile Asn His Lys Asp Phe
450                 455                 460

Leu Glu Ile Leu Gln Asn Ile Glu Gln Glu Gln Asp His Gln Lys Arg
465                 470                 475                 480
```

```
Ser Glu Leu Val Ser Gln Ala Ser Leu Tyr Leu Glu Thr Phe His Ile
            485                 490                 495

Ile Glu Pro Ile Tyr His Asp Ala Phe Gln Phe Ala Met Asn Lys Lys
            500                 505                 510

Leu Ser Asn Leu Gly Val Ser Pro Thr Gly Val Val Asp Phe Arg Tyr
        515                 520                 525

Ala Lys Glu Asn
    530

<210> SEQ ID NO 3
<211> LENGTH: 44
<212> TYPE: DNA
<213> ORGANISM: Artificial Sequence
<220> FEATURE:
<223> OTHER INFORMATION: 5' PCR primer

<400> SEQUENCE: 3
ataagaatgc ggccgccacc atgcgcaaga tatcagtggg aatc                    44

<210> SEQ ID NO 4
<211> LENGTH: 37
<212> TYPE: DNA
<213> ORGANISM: Artificial Sequence
<220> FEATURE:
<223> OTHER INFORMATION: 3' PCR primer

<400> SEQUENCE: 4
gcgccggatc ccattttcct tagcataacg gaagtcc                            37

<210> SEQ ID NO 5
<211> LENGTH: 22
<212> TYPE: PRT
<213> ORGANISM: Artificial Sequence
<220> FEATURE:
<223> OTHER INFORMATION: B-cell epitope

<400> SEQUENCE: 5

Asn Ile His Ser Tyr Pro Glu His Gln Lys Gln Glu Met Ala Gln
                5                  10                  15

Arg Gln Ala Tyr Ala Lys Lys
            20

<210> SEQ ID NO 6
<211> LENGTH: 14
<212> TYPE: PRT
<213> ORGANISM: Artificial Sequence
<220> FEATURE:
<223> OTHER INFORMATION: B-cell epitope

<400> SEQUENCE: 6

Gln Asn Ile Glu Gln Glu Gln Asp His Gln Lys Arg Ser Glu
                5                  10

<210> SEQ ID NO 7
<211> LENGTH: 9
<212> TYPE: PRT
<213> ORGANISM: Artificial Sequence
<220> FEATURE:
<223> OTHER INFORMATION: T-cell epitope

<400> SEQUENCE: 7

Arg Leu Leu Ser Glu Ile Ser Leu Val
                5
```